United States Patent [19]
Jones et al.

[11] Patent Number: 5,677,336
[45] Date of Patent: Oct. 14, 1997

[54] NON-STEROID ANDROGEN RECEPTOR ANTAGONIST COMPOUNDS AND METHODS

[75] Inventors: Todd K. Jones, Solana Beach; Lawrence G. Hamann, San Diego; Luc Farmer, San Diego; Michael G. Johnson, San Diego; Mark E. Goldman, San Diego, all of Calif.

[73] Assignee: Ligand Pharmaceuticals Incorporated, San Diego, Calif.

[21] Appl. No.: 141,492

[22] Filed: Oct. 21, 1993

[51] Int. Cl.$^6$ .................... A61K 31/04; A61K 31/05; A61K 31/085; A61K 31/12
[52] U.S. Cl. .................... 514/546; 514/544; 514/545; 514/676; 514/683; 514/684; 514/719; 514/727; 514/728; 514/731; 514/741
[58] Field of Search .................... 560/140; 568/306, 568/329, 330, 645, 705, 731, 743, 928; 514/544, 545, 546, 676, 683, 684, 719, 727, 728, 731, 741

[56] References Cited

U.S. PATENT DOCUMENTS

| | | | |
|---|---|---|---|
| 1,593,080 | 7/1926 | Jordan | 568/743 |
| 4,778,621 | 10/1988 | Isoyama et al. | 252/299.65 |
| 4,981,784 | 1/1991 | Evans et al. | 435/6 |
| 5,017,610 | 5/1991 | Imaki et al. | 514/546 |
| 5,071,773 | 12/1991 | Evans et al. | 435/6 |
| 5,128,479 | 7/1992 | Janssen et al. | 548/252 |
| 5,134,155 | 7/1992 | Connolly et al. | 514/403 |
| 5,135,940 | 8/1992 | Belanger et al. | 514/381 |

FOREIGN PATENT DOCUMENTS

| | | |
|---|---|---|
| 2133375 | 1/1972 | Germany . |
| 5-65243 | 3/1993 | Japan . |
| 9321145 | 10/1993 | WIPO . |

OTHER PUBLICATIONS

S. Antus et al, *Tetrahedron*, 42 (20):5637–5640 (1986).
S. Aoki et al, *J. Am. Chem. Soc.*, 110 (10):3296–3298 (May 11, 1988).
J. Chakravarty et al, *Proc. Indian Academy of Sciences, Section A*, 86A (3):317–325 (1977).
A.I. Chirko et al, *Chemical Abstracts*, 66 (21):8859, Abstract No. 94773s (May 22, 1967).
K. Das Gupta, *J. Indian Chemical Soc.*, 42(5):415–423 (1969).
C. Destabel et al, *J. Chem. Soc., Chemical Communications*, 8:596–568 (Apr. 15, 1992).
K. Laumen et al, *J. Chem. Soc., Chemical Communictions*, 1:49–51 (Jan. 1990).
M. Moreau et al, *Bulletin de la Societe Chimique de France*, 4:1362–1367 (1969).
H. Nagano et al, *Bulletin of the Chemical Society of Japan*, 65(9):2421–2426 (Sep. 1992).
K. Narasaka et al, *Tetrahedron*, 48(11):2059–2068 (Mar. 13, 1992).
K. Narasaka et al, *Chemistry Letters*, 8:1413–1416 (1991).
S. Pal et al, *J. Chem. Soc., Chemical Communications*, 22:1591–1593 (Nov. 15, 1991).
J.L. Reymond et al, *J. Am. Chem. Soc.*, 115(10):3909–3917 (May 19, 1993).
J.P. Yardley et al, *Experientia*, 34(9):1124–1125 (Sep. 15, 1978).
Riemschneider et al, *Chemical Abstracts*, vol. 78 (1973) 77564e.
Bolysheva et al, *Chemical Abstracts*, vol. 78 (1973) 42981m.
Rang et al, *Chemical Abstracts*, vol. 89 (1978) 162644c.
Pirkle et al, *Chemical Abstracts*, vol. 95 (1981) 42191e.
Agirbas et al, *Chemical Abstracts*, vol. 104 (1986) 207396v.
Kurusu et al, *Chemical Abstracts*, vol. 108 (1988) 130806b.
Gohndrone et al, *Chemical Abstracts*, vol. 117 (1992) 131372e.
Banik, B. K. et al., *J. Chem. Research(S)*, pp. 406–407, 1986.
Berry, N. M. et al., *Synthesis*, pp. 476–480, Jun. 1986.
Pal, S. et al., *Synthesis*, pp. 1073–1075, Nov. 1992.
Tanaka et al., *Agric. Biol. Chem.*, 54(1), 1990, pp. 121–123.
Berger, T. et al., *J. Steroid Biochem. Molec. Biol.*, 41:773 (1992).
Evans, R.M., *Science*, 240:889–95 (May 13, 1988).
Högberg, H. and Thomson, R.H., *J. Chem. Soc. Perkin Trans. 1*, pp. 1696–1701 (1976).
McConnell, O.J. et al., *Phytochemistry*, 21:2139–41 (1982).
Wall, M.E., et al., *J. of Natl. Prod.*, 52:1092–99 (Sep.–Oct. 1989).

*Primary Examiner*—Richard L. Raymond
*Attorney, Agent, or Firm*—Lyon & Lyon LLP

[57] ABSTRACT

Non-steroidal compounds which are high affinity, high specificity ligand antagonists for the androgen receptor are disclosed. Also disclosed are methods for employing the disclosed compounds for modulating processes mediated by the androgen receptor and for treating patients requiring androgen receptor antagonist therapy.

4 Claims, 3 Drawing Sheets

NON-STEROID ANDROGEN RECEPTOR ANTAGONIST COMPOUNDS AND METHODS

FIELD OF THE INVENTION

This invention relates to intracellular receptors and ligands therefor. More specifically, this invention relates to compounds which are non-steroidal androgen receptor antagonists, and methods for use of such compounds or ligands.

BACKGROUND OF THE INVENTION

A central problem in eukaryotic molecular biology continues to be the elucidation of molecules and mechanisms that mediate specific gene regulation in response to molecular inducers such as hormones. As part of the scientific attack on this problem, a great deal of work has been done in efforts to identify molecular inducers which are capable of mediating specific gene regulation.

Although much remains to be learned about the specifics of gene regulation, it is known that certain small molecule, non-peptide hormones and similarly acting vitamins and vitamin metabolites (collectively hereinafter called "hormones") modulate gene transcription by acting in concert with intracellular components, including intracellular receptors and discrete DNA promoter enhancer sequences known as hormone response elements (HREs).

These hormones, acting through, and as "ligands" for, their intracellular receptors, directly regulate hormone-responsive genes (and perhaps other important genes which are not directly hormone-responsive). Natural ligands for intracellular receptors are synthesized in the body or may be taken in as a component of food. It has also been shown that compounds other than the natural ligands can act upon intracellular receptors to regulate hormone-responsive genes. For example, some natural product derivatives and synthetic compounds also function as ligands for these receptors.

Intracellular receptors form a class of structurally-related genetic regulators scientists have named "ligand dependent transcription factors." Regulation of a gene by such factors requires both the intracellular receptor itself and a corresponding ligand which has the ability to selectively bind to the intracellular receptor in a way that affects gene activity. Until bound by a ligand, the intracellular receptor is unable to exert an effect on the gene. Hormone or other ligand molecules in the fluid surrounding a cell pass through the outer cell membrane by passive diffusion. Once inside the cell, the ligand binds to specific intracellular receptor proteins, creating a ligand/receptor complex. The binding of the ligand to its receptor induces a change in the shape of the intracellular receptor. This conformational change is believed to expose regions of the intracellular receptor that permit the intracellular receptor/ligand complex to bind to a specific subset of genes present in the cell's DNA in the cell nucleus.

The blueprint to build specific proteins is encoded in the DNA sequence of each gene. This blueprint is copied in a process referred to as "transcription," to give rise to the actual template for the production of specific proteins, messenger RNA or "mRNA". The mRNA then moves from the cell's nucleus into the cytoplasm and is translated, which results in the production of proteins encoded in the mRNA. Accordingly, a reduction in the transcription of mRNA reduces the production of the specific proteins.

Once the intracellular receptor/ligand complex binds to the specific site on the DNA, it alters the amount of the protein encoded by the gene that the cell is directed to produce, by altering the amount of mRNA transcribed by that gene. A ligand which binds an intracellular receptor and mimics the effect of the natural ligand is referred to as an "agonist" ligand. A ligand that inhibits the effect of the hormone is called an "antagonist." Intracellular receptors are referred to as "ligand-dependent transcription factors" because their activity is dependent upon the binding of their hormones or other ligands, which are necessary to drive the intracellular receptor into its active conformation.

The intracellular receptors form a large family of proteins that are closely related in structure. They are important drug targets, and many drugs currently on the market are ligands for these intracellular receptors. Not surprisingly, the structural similarity of the intracellular receptors often results in cross-reactivity between a drug and one or more intracellular receptors other than the desired target intracellular receptor. It is apparent, therefore, that there is a need to find alternative ligands (agonists and/or antagonists) which are readily available for therapeutic administration, have added specificity for particular intracellular receptors, and have increased activity.

Ligands to the androgen receptor are known to play an important role in prostatic hyperplasia, including cancer of the prostate and benign prostatic hypertrophy, male pattern baldness, acne, idiopathic hirsutism, Stein-Leventhal syndrome, mammary cancers and other health care problems. Thus, antagonists to testosterone, the endogenous hormone of the androgen receptor, are useful in treating chronic disorders such as those described above. In addition, the identification of compounds which interact with the androgen receptor, and thereby affect transcription of genes which are responsive to testosterone, would be of significant value, e.g., for therapeutic applications such as treatment of hormonally-responsive benign and malignant disorders.

Further, the identification of compounds which have good specificity for the androgen receptor, but which have less cross-reactivity for other intracellular receptors, would be of significant value since interaction of a ligand with other than the target intracellular receptors is known to result in significant undesirable pharmacological side effects. Accordingly, antagonists to the androgen receptor which do not display cross-reactivity with other intracellular receptors (e.g., gluccocorticoid receptor and mineralicorticoid receptor) will exhibit an improved therapeutic index.

A group of prenylated bromohydroquinones, called collectively cymopols, has been isolated and identified by several investigators using as a starting material the green marine alga*Cymopolia barbata* (L.) Lamouroux (Dasycladaceae). Among these, cymopol, $C_{16}H_{21}BrO_2$, is a crystalline phenol which has a bromogeranyl-hydroquinone or brominated monoterpene-quinol structure. As described by Högberg et al., J. C. S. Perkin I, 1696–1701 (1976), cymopol [2-bromo-5-(3,7-dimethylocta-2,6-dienyl) hydroquinone] and its monomethyl ether, $C_{17}H_{23}BrO_2$, have the following structures:

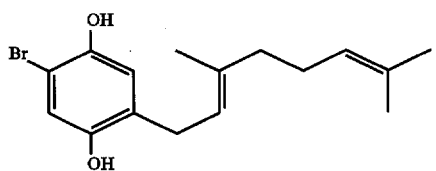

Cymopol

-continued

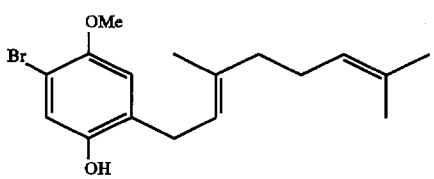

Cymopol monomethyl ether

Cyclocymopol [1-bromo-3-(4-bromo-2,5-dihydroxybenzyl)-2,2-dimethyl-4 methylene cyclohexane] and its monomethyl ether have also been obtained from *C. barbata*. See Högberg et al., supra. As described in McConnell et al., Phytochemistry, Vol. 21, No. 8, pp. 2139–41 (1982), *C. barbata* contains a mixture of optically active diastereomers of cyclocymopol, $C_{16}H_{20}Br_2O_2$, and cyclocymopol monomethyl ether, $C_{17}H_{22}Br_2O_2$, having the following structures:

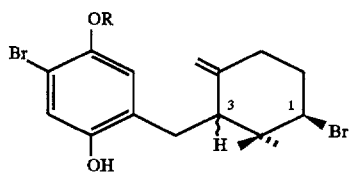

1a (R = H): 2a (R = Me): H(C-3)-pseudo-equatorial
1b (R = H): 2b (R = Me): H(C-3)-pseudo-axial (The above assumes the equatorial conformation for bromine at C-1).

Through silica gel chromatography of an ether-soluble extract of *C. barbata*, McConnell et al. were able to obtain a 1:1 mixture of α:β epimers of cyclocymopol. McConnell et al. also obtained a 3:1 mixture of α:β epimers of cyclocymopol monomethyl ether, which was enriched to a 4:1 mixture of the α:β epimers through purification techniques.

Wall et al., *J. Nat. Prod.*, Vol. 52, No. 5, pp. 1092-99 (1989), described additional diastereomeric cymopol compounds (cymobarbatol and 4-isocymobarbatol) which were determined to be highly active antimutagens. Wall et al. reported obtaining pure cymobarbatol compounds, but were unable to obtain stable cyclocymopol fractions. Apparently, however, the forms of cyclocympol and cyclocymopol monomethyl ether obtained by Högberg et al., supra, were pure forms of formulae 1b and 2b above.

The publications and references referred to above and hereafter in this specification are expressly incorporated herein by reference.

SUMMARY OF THE INVENTION

The present invention is directed to compounds, compositions, and methods for modulating processes mediated by the androgen receptor. More particularly, the invention relates to non-steroidal compounds which are high affinity, high specificity ligands for the androgen receptor (AR). These compounds exhibit AR antagonist activity, and modulate processes mediated by AR. Accordingly, the invention also relates to methods for modulating processes mediated by AR employing the compounds disclosed. Examples of compounds used in and forming part of the invention include synthetic cyclocymopol analogs, and semisynthetic derivatives of natural cyclocymopols. Pharmaceutical compositions containing the compounds disclosed are also within the scope of this invention. Also included are methods for identifying or purifying AR by use of the compounds of this invention.

DEFINITIONS

In accordance with the present invention and as used herein, the following terms are defined with the following meanings, unless explicitly stated otherwise.

The term alkyl refers to straight-chain, branched-chain, cyclic structures, and combinations thereof.

The term "aryl" refers to aromatic groups which have at least one ring having a conjugated pi electron system and includes carbocyclic aryl, heterocyclic aryl and biaryl groups, all of which may be optionally substituted, being preferably phenyl or phenyl substituted by one to three substituents, such substituents being advantageously lower alkyl, hydroxy, lower alkoxy, lower acyloxy, halogen, cyano, trihalomethyl, lower alcylamino, or lower alkoxycarbonyl.

Carbocyclic aryl groups are groups wherein the ring atoms on the aromatic ring are carbon atoms. Carbocyclic aryl groups include monocyclic carbocyclic aryl groups and optionally substituted naphthyl groups.

Heterocyclic aryl groups are groups having from 1 to 3 heteroatoms as ring atoms in the aromatic ring with the remainder of the ring atoms being carbon atoms. Suitable heteroatoms include oxygen, sulfur, and nitrogen, and suitable heterocyclic aryl groups include furanyl, thienyl, pyridyl, pyrrolyl, N-lower alkyl pyrrolyl, pyrimidyl, pyrazinyl, imidazolyl, and the like, all optionally substituted.

The term "aralkyl" refers to an alkyl group substituted with an aryl group. Suitable aralkyl groups include benzyl and the like, and may be optionally substituted.

The term "lower" referred to herein in connection with organic radicals or compounds respectively defines such with up to and including 7, preferably up to and including 4 and advantageously one or two, carbon atoms. Such groups may be straight chain or branched.

BRIEF DESCRIPTION OF THE DRAWINGS

The present invention may be better understood, and its advantages appreciated by those skilled in the art by referring to the accompanying drawings wherein.

DETAILED DESCRIPTION OF EMBODIMENTS OF THE INVENTION

Figure 1:
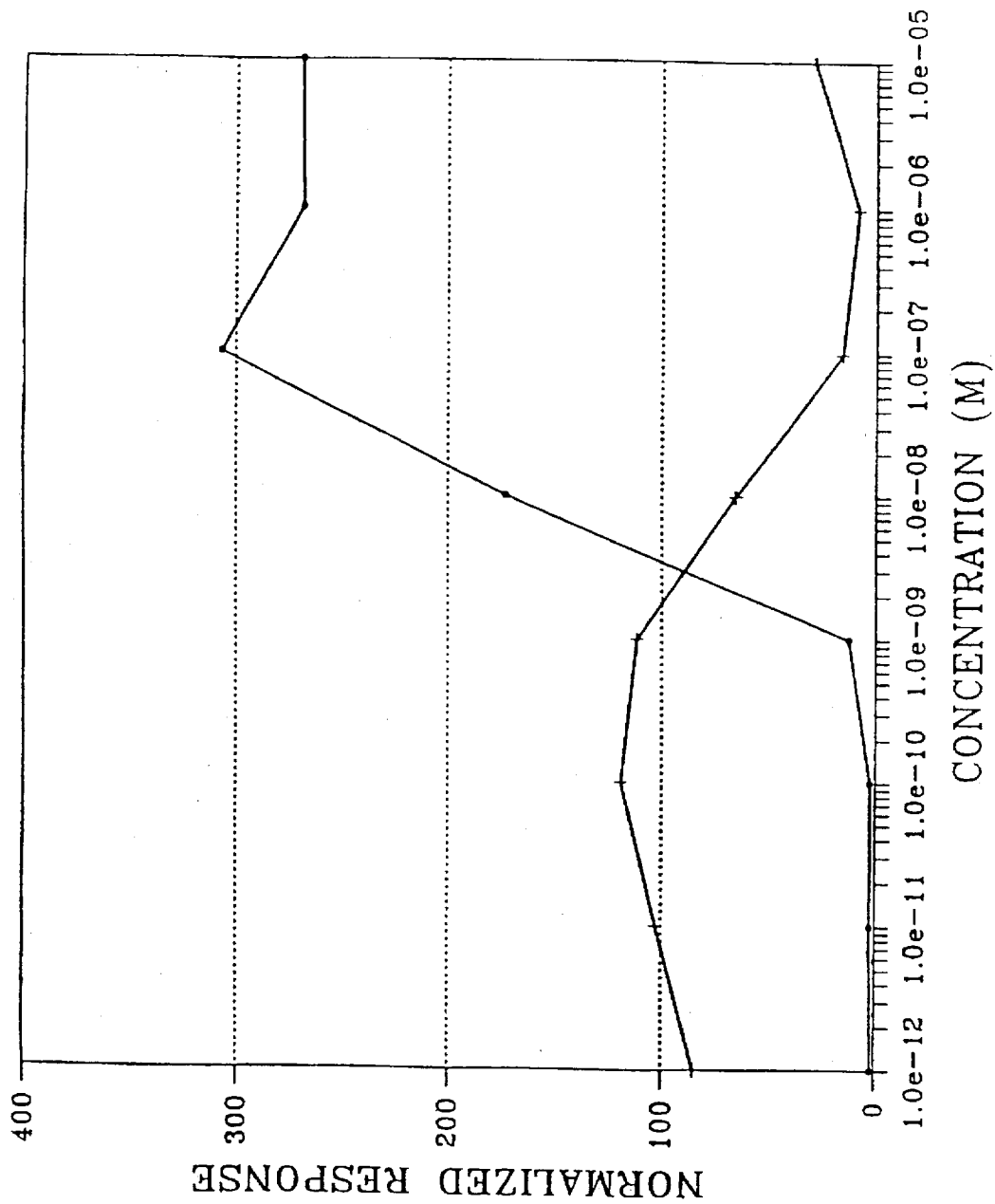
FIG. 1 presents activation profiles for analysis of androgen receptor by increasing concentrations of dihydrotestosterone (DHT) (•) and the antagonist dose response profile of 2Hydroxy-flutamide (+) at a constant concentration of 5×10–9M DHT.

Cyclocymopols useful in this invention are defined as those having the formulae:

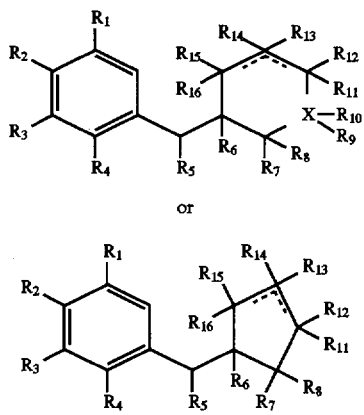

wherein:

the dotted lines in the structure depict optional double bonds;

X is carbon, oxygen, or nitrogen;

$R_1$ is $R_{17}$, —$OR_{17}$, —$N(R_{17})(R_{17'})$, —$SR_{17}$, fluorine, chlorine, bromine, or —$NO_2$;

$R_{17}$ and ($R_{17'}$), each independently, are hydrogen, saturated or unsaturated $C_1$–$C_6$ alkyl, $C_3$–$C_7$ cycloalkyl, $C_5$–$C_7$ aryl, or C7 aralkyl, said alkyl groups being branched or straight-chain;

$R_2$ is —$NO_2$, —$N(OH)R_{17}$, fluorine, chlorine, bromine, iodine, $R_{17}$, —$N(R_{17})(R_{17'})$, —$SR_{17}$, —$S(O)$—$R_{17}$, —$S(O)_2$—$R_{17}$, —$CH_2OH$, —$C(O)$—H, —$C(O)CH_3$, —$C(O)$—$OCH_3$, —$C$=$CH_2$, —$C$=$CH$—$C(O)$—$OCH_3$, or $R_{18}$;

$R_{18}$ and ($R_{18'}$), each independently, are hydrogen, saturated or unsaturated $C_1$–$C_6$ alkyl, $C_3$–$C_7$ cycloalkyl, $C_5$–$C_7$ aryl, or $C_7$ aralkyl, said alkyl groups being branched or straight-chain which optionally may contain hydroxyl, aldehyde, ketone, nitrile, or ester groups;

$R_3$ is $R_{17}$ or —$OR_{17}$;

$R_4$ is hydrogen, —$OR_{17}$, —$OC(O)R_{17}$, —$OC(O)OR_{17}$, —$OC(O)N(R_{17})(R_{17'})$, —$OS(O)_2R_{17}$, or —$OS(O)$—$R_{17}$;

$R_5$ is hydrogen or $OR_{17}$;

$R_6$ is $R_{17}$;

$R_7$ and $R_8$, each independently, are $R_{18}$, or $R_7$ and $R_8$ together are a carbocyclic 3–8 member ring;

$R_9$ and $R_{10}$, each independently, are chlorine, bromine, or $R_{17}$, or $R_9$ and $R_{10}$ combined are =O, except when X=O, $R_9$ and $R_{10}$ are not present, and when X is N, then $R_{10}$ is not present, or $R_9$ and $R_{10}$ together are joined in a carbocyclic 3–8 member ring;

$R_{11}$ and $R_{12}$, each independently, are —$OR_{17}$, $R_{18}$, are =O, or are =$CH_2$, except when $R_{11}$ is attached to an sp$^2$ carbon atom in the ring, then $R_{12}$ is not present and $R_{11}$ is $R_{18}$, or $R_{11}$ and $R_{13}$ together are joined in a carbocyclic 3–8 member ring or are —O—to form an epoxide;

$R_{13}$ and $R_{14}$, each independently, are —$OR_{17}$ or $R_{18}$, except when $R_{13}$ is attached to an sp$^2$ carbon atom in the ring, then $R_{14}$ is not present and $R_{13}$ is —$OR_{17}$ or $R_{18}$;

$R_{15}$ and $R_{16}$, each independently, are $R_{18}$ or $OR_{17}$, or $R_{15}$ and $R_{16}$ together are —$CH_2$—O—forming an epoxide, or $R_{15}$ and $R_{16}$ combined are =O or =$C(R_{18})(R_{18'})$, except when $R_{15}$ is hydroxyl, then $R_{16}$ is not hydroxyl, and when $R_{15}$ is attached to an sp$^2$ carbon atom in the ring, then $R_{16}$ is not present, or $R_{15}$ and $R_{16}$ together are joined in a carbocyclic 3–8 member ring.

Representative compounds and derivatives according to the present invention include the following:

1-Methylidene-6-(3'-nitrophenyl)methyl-5,5-dimethylcyclohex-2-ene;

(1S,3S)-1-Hydroxy-2-methylidene-3-(2'-hydroxy-4'-bromo-5'-methoxyphenyl)methyl-4,4-dimethylcyclohexane;

1-Methylidene-6-(2'-hydroxyphenyl)methyl-5,5-dimethylcyclohex-2-ene;

1-Methylidene-2-(2'-hydroxyphenyl)methyl-5,5-dimethylcyclohexane;

(4S,6S)-1-Methylidene-4-bromo-5-(2'-acetoxy-4'-bromo-5'-methyoxyphenyl)methyl-5,5 -dimethylcyclohex-2-ene;

1-Methylidene-6-(2'-acetoxy-4'-bromo-5'-methoxyphenyl)methyl-5,5-dimethylcyclohex-2-ene;

2-(4'-Nitrophenyl)methylcyclohexan-1-one;

8-(2'-Acetoxy-4'-bromo-5'-methoxyphenyl)methyl-5,7,7-trimethylspiro[2.5]oct-4-ene;

trans-2-(4'-Nitrophenyl)methylcyclohexan-1-ol;

(1S,3S)-1-Hydroxy-2-methylidene-3-(2'-hydroxy-4'-bromo-5'-methoxyphenyl)methyl-1,4,4-trimethylcyclohexane;

1-Methylidene-2-(2'-hydroxy-4'-bromo-5'-methoxyphenyl)methyl-3,3-dimethylcyclopentane;

(5R,6S)-1 -Methylidene-6-(2'-acetoxy-4'-bromo-5'-methoxyphenyl)methyl-5-methylcyclohex-2-ene;

1-Methylidene-2-(2'-hydroxy-4'-bromo-5'-methoxyphenyl)methyl-3,3-dimethylcyclohexane;

(2R)-1-Methylidene-2-(2'-hydroxy-4'-bromo-5'-methoxyphenyl)methyl-3,3-dimethylcyclohexane;

(5R,6S)-1-Methylidene-6-(2'-acetoxy-4'-bromo-5'-methoxyphenyl)methyl-3,5-dimethylcyclohex-2-ene;

(1R,3S)-1-Hydroxy-2-methylidene-3-(2'-hydroxy-4'-bromo-5'-methoxyphenyl)methyl-1,4,4-trimethylcyclohexane;

trans-1-Methyl-2-(2'-hydroxy-4'-bromo-5'-methoxyphenyl)methylcyclohexan-1-ol;

(1R,3R)-1 -Hydroxy-2-methylidene-3-(2'-hydroxy-4'-bromo-5'-methoxyphenyl)methyl-4,4-dimethylcyclohexane;

cis-1-Methylidene-2-(2'-hydroxy-4'-bromo-5'-methoxyphenyl)methyl-3,3,5-trimethylcyclohexane;

1-Methylidene-6-(3 '-methyl-4'-nitrophenyl)methyl-5,5-dimethylcyclohex-2-ene;

1-Methylidene-6-(4'-nitro-3'-methylphenyl)methyl-3,5,5-trimethylcyclohex-2-ene;

2-(4'-Nitrophenyl)methyl-3,3-dimethylcyclohexan-1-one;

1-Methylidene-6-(2'-hydroxy-4'-bromo-5'-methoxyphenyl)methyl-5,5-dimethylcyclohex-2-ene;

(2S)-1-Methylidene-2-(2'-hydroxy-4'-bromo-5'-methoxyphenyl)methyl-3,3-dimethylcyclohexane; and 2-(2'-Hydroxy-4'-bromo-5'-methoxyphenyl)methylcyclohex-1-one.

Compounds comprising the class of synthetic cyclocymopol analogs and derivatives disclosed herein can be obtained by routine chemical synthesis by those skilled in the art, e.g., by modification of the cyclocymopol compounds disclosed or by a total synthesis approach.

The invention will be further illustrated by reference to the following non-limiting Examples. All parts and percentages are expressed as parts by weight unless otherwise indicated.

EXAMPLE 1

Synthetic and semisynthetic cyclocymopol analogs have been prepared which display antagonist activity for the intracellular receptor for androgen. Representative analogs of the present invention are prepared according to the following illustrative synthetic schemes and illustrative Examples.

Synthesis of Aromatic Subunit

2-Acetoxy-5-methoxybenzaldehyde (1):

To a flame-dried 50 mL round-bottomed flask containing 10.00 g (65.7 mmol) 2-hydroxy-5-methoxybenzaldehyde in 10 mL dry pyridine at 0° C. under nitrogen atmosphere was added 7 mL acetic anhydride. The reaction mixture was then allowed to warm to room temperature and continually stirred until thin-layer chromotography (TLC) analysis indicated complete consumption of starting material (50 min). Ethyl acetate (150 mL) was added, and the mixture was then transferred to a separatory funnel and successively washed with 1N HCl (3×50 mL), saturated aqueous $NaHCO_3$ (1×50 mL), and brine (1×50 mL), dried over $Na_2SO_4$, and concentrated under reduced pressure to give 12.41 g (97%) of the acetylated phenol as a white solid. The product thus obtained was homogenous by TLC. (Rf 0.41, 2:1 hexane/ethyl acetate), and was carried on to the next step without further purification.

2-Acetoxy-4-bromo-5-methoxybenzaldehyde (2):

To a 500 mL round-bottomed flask containing a solution of 20.0 g (168.1 mmol, 3.26 equiv) potassium bromide and 3.21 mL (10.0 g, 62.6 mmol, 1.21 equiv) bromine in 200 mL water at room temperature was added 10.00 g (51.5 mmol, 1.0 equiv) 2-acetoxy-5-methoxybenzaldehyde (1) as a finely divided white powder, portionwise over a period of 35 min. After 18 h stirring at room temperature, the reaction mixture was filtered under vacuum using a Büchner funnel to give 10.59 g (89%) of the aryl bromide as a pale yellow solid (Rf0.45, 2:1 hexanes/ethyl acetate). The product thus obtained was of greater than 98% purity by $^1H$ NMR, and homogenous by TLC, and was carded on to the next step without further purification. A portion of the crude product was recrystallized from 5:1 ether/hexanes to give white needles. $^1H$ NMR (400 MHz, $CDCl_3$) δ2.37 (s, 3H, $COCH_3$), 3.93 (s, 3H, $OCH_3$), 7.36 and 7.46 (2s, 2×1H, Ar—H), 10.08 ppm (s, 1H, CHO).

2-Hydroxy-4-bromo-5-methoxybenzaldehyde

To a 200 mL round-bottomed flask containing 6.90 g (25.3 mmol) 2 acetoxy-4-bromo-5-methoxybenzaldehyde (2) in 100 mL of 1% aqueous methanol at room temperature was added 5 g $K_2CO_3$, and the mixture was allowed to stir at room temperature for 1 h, at which time TLC analysis indicated complete consumption of starting material and the presence of a slightly more polar compound as the only detectable product. The reaction mixture was then neutralized to pH 5 with the addition of 1N HCl, and the solvent was subsequently removed under diminished pressure. The residue was then dissolved in ethyl acetate (200 mL), washed successively with 1N HCl (1×50 mL), saturated aqueous $NaHCO_3$ (1×50 mL), and brine (1×50 mL), dried over $NA_2SO_4$, and concentrated under diminished pressure to give 4.97 g (85%) of the bromophenol as a brownish-red oily solid. A portion of this crude material was recrystallized from 2:1 hexanes/ethyl acetate to give white needles. $^1H$ NMR (400 MHz, $CDCl_3$) δ3.89 (s, 3H, $OCH_3$), 6.97 and 7.27 (2s, 2×1H, Ar—H), 9.83 (s, 1H, OH), 10.71 ppm (s, 1H, CHO). The remainder of the material was carded on to the next step without further purification.

2-(tert-Butyl)dimethylsilyloxy-4-bromo-5-methoxybenzaldehyde (4):

To a flame-dried 100 mL round-bottomed flask containing 2.76 g (11.95 mmol) 2-hydroxy-4-bromo-5-methoxybenzaldehyde (3) in 50 mL anhydrous dichloromethane under nitrogen atmosphere at room temperature was added 2.03 g (29.88 mmol, 2.50 equiv) imidazole, 2.25 g (14.94 mmol, 1.25 equiv) (tert-butyl)-dimethylchlorosilane, and 4-N,N'-dimethyl propyleneurea (DMAP) (100 mg, catalytic). The mixture was allowed to stir at room temperature for 75 rain, at which time TLC. analysis indicated complete consumption of starting material, and the formation of a less polar product (Rf 0.75, 2: I hexanes/ethyl acetate). The reaction mixture was then poured into a separatory funnel containing 50 mL dichloromethane and 50 mL saturated aqueous $NH_4Cl$, the layers were separated, and the organic phase was washed with 50 mL brine, dried over $Na_2SO_4$, and concentrated under diminished pressure to give 4.13 g (quantitative) of the silylated bromophenol as an off-white solid, a portion of which was recrystallized from 3:1 hexanes/ether to give an amorphous white solid. $^1H$ NMR (400 MHz, CDCl ) δ0.27 [s, 6H, $Si(CH_3)_2$], 1.02 [s, 9H, $SiC(CH_3)_3$], 3.89 (s, 3H, $OCH_3$), 7.14 (s, 1H, 6-H), 7.28 (s, 1H, 3-H), 10.35 ppm (s, 1H, CHO); $^{13}C$ NMR (100.61 MHz, $CDCl_3$) δ-4.4, 18.3, 25.7, 56.6, 108.9, 120.1, 125.6, 126.5, 151.0, 152.9, 189.1 ppm.

2-(tert-Butyl)dimethylsilyloxy-4-bromo-5-methoxybenzyl alcohol (5):

To a flame-dried 200 mL round-bottomed flask containing 4.10 g (13.14 mmol) 2-(tert-butyl)dimethylsilyloxy-4-bromo-5-methoxybenzaldehyde (4) in 100 mL anhydrous methanol at 0° C. was added 0.50 g (13.15 mmol, 1.0 mol equiv) $NaBH_4$ over a period of 3 min. After 20 min at 0° C., TLC. analysis indicated complete consumption of starting material, and the formation of a more polar product (Rf 0.42, 2:1 hexanes/ethyl acetate). Water (75 mL) was added, and the methanol was removed by rotary evaporation. The resultant aqueous residue was extracted with ethyl acetate (2×100 mL), and the combined organic layers were dried over $Na_2SO_4$, and concentrated under diminished pressure. Purification by flash column chromatography (silica gel, hexanes/ethyl acetate, 5:1) afforded 4.10 g (98%) of the benzylic alcohol as a white solid. $^1H$ NMR (400 MHz, $CDCl_3$) δ0.23 [s, 6H, $Si(CH_3)_2$], 1.00 [s, 9H, $SiC(CH_3)_3$], 3.86 (s, 3H, $OCH_3$), 4.61 (s, 2H, $CH_2OH$), 6.92 (s, 1H, 6-H), 6.97 ppm (s, 1H, 3-H).

2-(tert-Butyl)dimethylsilyloxy-4-bromo-5-methoxybenzyl bromide (6):

To a flame-dried 100 mL round-bottomed flask containing triphenylphosphine (1.27 g, 4.84 mmol, 1.05 equiv) in 25 mL anhydrous dimethylformamide (DMF) at 0° C. under nitrogen atmosphere was added bromine (0.24 mL, 4.84 mL, 1.05 equiv, plus enough extra to cause a persistent reddish tint to the solution, 1 drop) through an additional funnel. To this reaction mixture was added 2-(tert-butyl) dimethylsilyloxy-4-bromo-5-methoxybenzyl alcohol (5) through the addition funnel at a steady rate over 30 min, as a solution in 10 mL DMF. The reaction mixture was allowed to stir at 0° C. for 60 min, at which time TLC. analysis indicated complete consumption of starting material, and the formation of a less polar product (Rf 0.81, 2:1 hexanes/ethyl acetate). Hexane (100 mL) was then added, and the contents of the flask were transferred to a separatory funnel containing 50 mL of saturated aqueous NH₄Cl, rinsing with an additional 50 mL hexane and 10 mL water. The layers were separated, and the organic phase was washed with 20 mL 10% Na₂S₂O₃, dried over Na₂SO₄, and concentrated under diminished pressure. Purification by trituration at 0° C. (2×30 mL ea. hexanes) to remove residual triphenylphosphine oxide, followed by flash column chromatography (silica gel, hexanes/ethyl acetate, gradient elution) afforded 1.51 g (80%) of the benzylic bromide as a colorless, viscous oil, which solidified upon standing. ¹H NMR (400 MHz, CDCl₃) δ0.27 [s, 6H, Si(CH₃)₂], 1.04 [s, 9H, SiC(CH₃)₃], 3.84 (s, 3H, OCH₃), 4.46 (s, 2H CH₂Br), 6.87 and 7.01 ppm (2s, 2×1H, Ar—H).

2-(tert-Butyl)dimethylsilyloxybenzaldehyde (7):

This compound was prepared from salicylaldehyde (3.00 g, 24.1 mmol) in the manner previously described for the synthesis of silyl ether (4), affording 4.23 g (74%) of the silylated phenol as a colorless oil. ¹H NMR (400 MHz, CDCl₃) δ0.28 [s, 6H, Si(CH₃)₂], 1.03 [s, 9H, SiC(CH₃)₃], 6.88 (d, 1H, J=8.5 Hz, Ar—H), 7.03 (dd, 1H, J=7.4 Hz, Ar—H), 7.46 (ddd, 1H, J=8.6, 7.4, 2.0 Hz, Ar—H), 7.81 (dd, 1H, J=7.7, 1.9 Hz, Ar—H), 10.47 ppm (s, 1H, CHO).

2-(tert-Butyl)dimethylsilyloxybenzyl alcohol (8):

This compound was prepared from 2-(tert-butyl)dimethylsilyloxybenzaldehyde (7) (4.23 g, 17.9 mmol) in the manner previously described for the synthesis of benzyl alcohol 5, affording 2.81 g (66%) of the silyloxybenzyl alcohol as a pale yellow oil. ¹H NMR (400 MHz, CDCl₃) δ0.26 [s, 6H, Si(CH₃)₂], 1.02 [s, 9H, SiC(CH₃)₃], 4.68 (d, 2H, J=6.3 Hz, CH₂OH), 6.81 (d, 1H, J=6.3 Hz, Ar—H), 6.95 (dd, 1H, J=7.1, 7.1 Hz, Ar—H), 7.17 (ddd, 1H, J=9.5, 7.8 1.7 Hz, Ar—H), 7.30 ppm (dd, 1H, J=5.8, 1.6 Hz, Ar—H).

2-(tert-Butyl)dimethylsilyloxybenzyl bromide (9):

This compound was prepared from 2-(tert-butyl)dimethylsilyloxybenzyl alcohol (8) (2.81 g, 11.8 mmol) in the manner previously described for the synthesis of benzyl bromide 6, affording 1.14 g (32%) of the silyloxybenzyl bromide as a colorless oil. 1H NMR (400 MHz, CDCl₃) δ0.30 [s, 6H, Si(CH₃)₂], 1.07 [s, 9H, SiC(CH₃)₃], 4.54 (s, 2H, CH₂Br), 6.83 (d, 1H, J=6.2 Hz, Ar—H), 6.93 (dd, 1H, J=7.1, 7.1 Hz, Ar—H), 7.19 (ddd, 1H, J=9.4, 7.9, 1.6 Hz, Ar—H) 7.34 ppm (dd, 1H, J=5.8, 1.6 Hz, Ar—H).

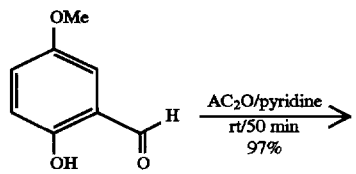

1

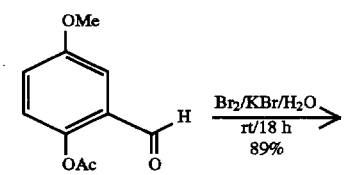

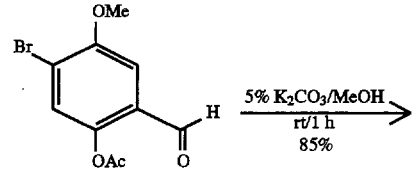

2

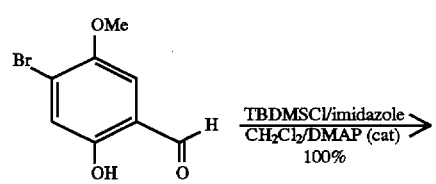

3

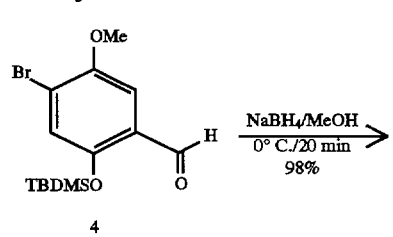

4

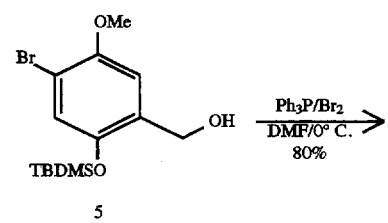

5

6

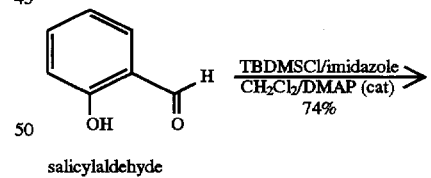

salicylaldehyde

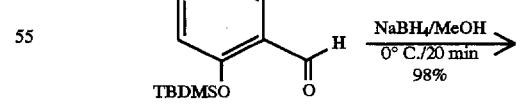

7

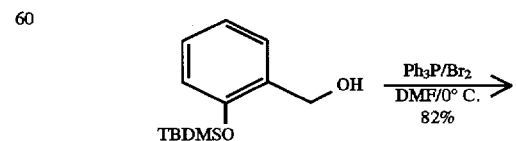

8

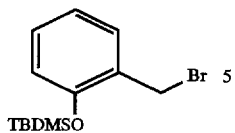

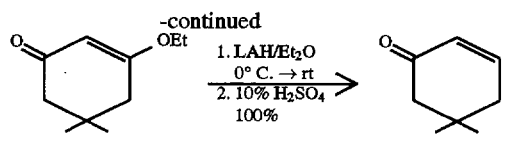

EXAMPLE 2

Synthesis of Aliphatic Subunits

3-Ethoxy-5,5-dimethylcyclohex-2-en-1-One (10):

To a flame-dried 1 L round-bottomed flask containing 15.0 g (107 mmol) 5,5-dimethylcyclohexane-1,3-dione and 120 mL absolute ethanol in 300 mL anhydrous benzene under nitrogen atmosphere was added 750 mg p-toluenesulphonic acid monohydrate (catalytic). The flask was fitted with a Dean Stark trap for removal of water, and a reflux condenser, and the mixture was heated to reflux for 9 h. Upon cooling to room temperature, the solvent was removed by rotary evaporation, and the residue was dissolved in 300 mL ethyl acetate. The organic solution was then washed successively with 10% aqueous NaOH (2 x 100 mL), water (1×100 mL), and brine (1×100 mL), dried over $Na_2SO_4$, and concentrated under diminished pressure to give 16.5 g (92%) of the keto-enol ether as a pale yellow oil (Rf 0.24, 2:1 hexanes/ethyl acetate) of greater than 98% purity by $^1H$ NMR. $^1H$ NMR (400 MHz, $CDCl_3$) δ1.08 (s, 6H, geminal-$CH_3$'s), 1.38 (dd, 3H, $OCH_2CH_3$), 2.21 and 2.28 (2s, 2×2H, 6-H, 4H), 3.90 (q, 2H, $OCH_2CH_3$), 5.32 ppm (s, 1H, 2-H).

5.5-Dimethylcyclohex-2-en-1-one (11):

To a flame-dried 100 mL round-bottomed flask containing lithium aluminum hydride (0.95 g, 24.4 mmol, 0.5 mol equiv) in 35 mL anhydrous ether under nitrogen atmosphere at 0° C. was added 8.20 g (48.7 mmol) 3-ethoxy-5,5-dimethylcyclohex-2-en-1-one (10) portionwise through a syringe as a solution in 10 mL anhydrous ether. The reaction mixture was allowed to warm to room temperature, and after 4h, T.L.C. analysis indicated complete consumption of starting material. The reaction mixture was then cooled to 0° C. before the cautious addition of 50 mL water, and the contents of the flask were then poured into a 500 mL Edenmeyer flask containing 150 mL ice-cold 10% $H_2SO_4$. The mixture was then extracted with ether (2×200 mL), and the combined organics were washed successively with water (100 mL), and saturated aqueous $NaHCO_3$ (100 mL), dried over $Na_2SO_4$, and concentrated under diminished pressure to give 6.05 g (quantitative) of the dimethylenone (Rf 0.55, 2:1 hexane/ethyl acetate). $^1H$ NMR (400 MHz, $CDCl_3$) δ1.05 (s, 6H, geminal-$CH_3$'s), 2.23 (dd, 2H, 4-H), 2.28 (s, 2H, 6-H), 6.03 (ddd, 1H, 2-H), 6.87 ppm (ddd, 1H, 3-H).

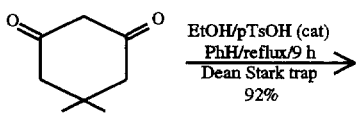

dimedone

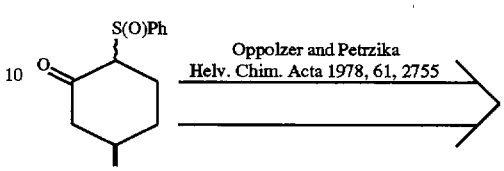

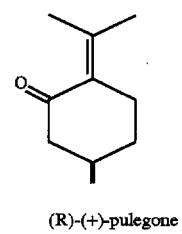

(R)-(+)-pulegone

SYNTHESIS OF ANALOGS

EXAMPLE 3

6-[2'-(tert-Butyl)dimethylsilyloxy-4'-bromo-5'methoxyphenyl]methyl-5,5-dimethylcyclohex-2-en-1-one (13):

To a flame-dried 50 mL round-bottomed flask containing diisopropylamine (0.188 mL, 1.34 mmol, 1.1 equiv) in 10 mL anhydrous tetrahydrofuran (THF) at −78° C. under nitrogen atmosphere was added n-butyllithium (0.58 mL of a 2.2 M solution in hexanes, 1.28 mmol, 1.05 equiv). After 20 min at −78° C., 5,5-dimethylcyclohex-2-en-one (11) (0.151 g, 1.22 mmol) was added as a solution in 1 mL of THF, and the reaction mixture was allowed to stir at that temperature for 15 min, at which time the cooling bath was removed. When the temperature of the reaction mixture (monitored using a thermocouple probe) reached −5° C., 2-(tert-butyl)dimethylsilyloxy-4-bromo-5-methoxybenzyl bromide (6) (1.00 g, 2.44 mmol, 2.0 equiv) was added all at once as a solution in 2 mL THF. The reaction mixture was then allowed to warm to room temperature, and after 3 h, T.L.C. analysis indicated complete consumption of the enone starting material, and the formation of a product of intermediate polarity with respect to the two starting components (Rf 0.59, 2:1 hexanes/ethyl acetate), and the reaction was quenched by the addition of 5 mL saturated aqueous $NH_4Cl$. The contents of the flask were transferred to a separatory funnel, and extracted with 60 mL ethyl acetate, and the resultant organic phase was washed with 30 mL brine, dried over $Na_2SO_4$, and concentrated under diminished pressure. Purification by flash column chromatography (silica gel, hexanes/ethyl acetate, gradient elution) afforded 0.459 g (83%) of the benzylated enone as a colorless, viscous oil, which solidified on standing. $^1H$ NMR (400 MHz, $CDCl_3$) δ0.21 and 0.23 [2s, 2×3H, $Si(CH_3)_2$], 1.00 [s, 9H, $SiC(CH_3)_3$], 1.02 and 1.03 (2s, 2×3H, geminal-$CH_3$'s), 2.25 an 2.32 (ddd of ABq, 2H, 4-H), 2.51 (dd, 1H, 6-H), 2.78 and 2.88 (d of ABq, 2H, benzylic-$CH_2$), 3.80 (s, 3H, $OCH_3$), 5.96 (ddd, 1H, 2-H), 6.68 (s, 1H, 6'-H), 6.77 (ddd, 1H, 3-H), 6.94 ppm (s, 1H, 3'-H).

2-[2'-(tert Butyl)dimethylsilyloxy-4-bromo-5'-methoxyphenyl]methyl-3,3-dimethyl-cyclohexanone (14):

To a flame-dried round-bottomed flask containing 6-[2'-(tert-butyl)dimethylsilyloxy-4'-bromo-5'-methoxyphenyl]methyl-5,5-dimethylcyclohex-2-en-1-one (13) (0.154 g, 0.454 mmol) in 22 mL ethyl acetate (which had been pre-dried over $K_2CO_3$) at room temperature was added 20 mg 5% palladium on carbon, and after flushing / evacuating the vessel 3 times with nitrogen, a hydrogen atmosphere was introduced and maintained by use of a balloon. After 24 h, the flask was again flushed several times with nitrogen, and the contents of the flask were filtered, rinsing with an additional 100 mL ethyl acetate. Rotary evaporation of the solvent afforded 0.156 g (quantitative) of the saturated benzylic ketone as a colorless, viscous oil (Rf 0.67, 2:1 hexanes/ethyl acetate). $^1$H NMR (400 MHz, $CDCl_3$) $\delta$0.22 and 0.25 [2s, 2×3H, $Si(CH_3)_2$], 0.87 and 1.12 (2s, 2×3H, geminal-$CH_3$'s), 1.01 [s, 9H, $SiC(CH_3)_3$], 3.71 (s, 3H, $OCH_3$), 6.79 (s, 1H, 6'-H), 6.91 ppm (s, 1H, 3'-H).

1-Methylidene-2-(2'-hydroxy-4'-bromo5'-methoxyphenyl)methyl-3,3-dimethylcyclohexane (16):

To a flame-dried 50 mL round-bottomed flask containing 2-[2'-(tert-butyl)dimethylsilyloxy-4'-bromo-5'-methoxyphenyl]methyl-3,3-dimethylcyclohexanone (14) (0.130 g, 0.28 mmol) in 5 mL anhydrous THF at −78° C. under nitrogen atmosphere was added (trimethyl)silylmethyllithium (0.420 mL of a 1.0 M solution in pentane, 0.42 mmol, 1.50 equiv). An immediate change from colorless to a yellow reaction solution was observed, and TLC analysis at that time indicated complete consumption of starting material, and the formation of a less polar product (Rf 0.79, 2:1 hexanes lethyl acetate), and the reaction was subsequently quenched with 4 mL saturated aqueous $NH_4Cl$. Ethyl acetate (30 mL) extraction of the reaction mixture, drying over $Na_2SO_4$, and concentration under diminished pressure gave 0.152 g (quantitative) of a crude product (15), which appeared to be a single diastereomer of the ketone addition product by 1H NMR analysis. A portion of this crude intermediate (0.015 g, 0.028 mmol) was placed in a 10 mL Nalgene vial containing 2 mL THF, 0.2 mL of a premade HF/pyridine complex was added, and the mixture was allowed to stir at room temperature for 32 h, at which time TLC. analysis indicated complete consumption of starting material, and formation of a more polar product, having passed through a most polar intermediate (confirmed as the desilylated phenol by 1H NMR). The contents of the reaction vessel were transferred to a separatory funnel containing 20 mL ethyl acetate and 10 mL 1.0M $NaHSO_4$. The layers were separated, and the resultant organic phase was washed with 10 mL brine, dried over $Na_2SO_4$, and concentrated under reduced pressure. Purification by flash column chromatography (silica gel, hexanes/ethyl acetate, gradient elution) afforded 8.7 mg (92%) of the phenolic olefin as a colorless oil. 1H NMR (400 MHz, $CDCl_3$) $\delta$0.97 and 1.00 (2s, 2×3H, geminal-$CH_3$'s), 2.65 and 2.80 (d of ABq, $J_{AB}$=14.1 Hz, $J_A$=10.9 Hz, $J_B$=3.5 Hz, 2H, benzylic-$CH_2$), 3.80 (s, 3H, $OCH_3$), 4.36 (d, 1H, J=1.0 Hz) and 4.64 (s, 1H) [methylidene-$CH_2$], 6.59 (s, 1H), 6.94 ppm (s, 1H, 3'-H); $^{13}$C NMR (100.61 MHz, $CDCl_3$) $\delta$5 23.5, 26.7, 28.1, 28.4, 32.4, 35.2, 36.1, 54.3, 57.0, 108.3, 110.3, 115.0, 120.1, 128.8, 148.0, 148.5, 150.0 ppm. [Compound 16 is hereinafter also referred to as COMPOUND "M" or 120019]

EXAMPLES 4–5

1-Methylidene-6-(2'-acetoxy-4'-bromo-5'-methoxyphenylmethyl-5,5-dimethylcyclo-hex-2-ene (17):

This compound was prepared from 6-[2'-(tert-butyl)dimethylsilyloxy-4'-bromo-5'-methoxyphenyl]methyl-5,5-dimethylcyclohex-2-en-1-one (13) (0.075 g, 0.166 mmol) in the manner previously described for olefin 16, with the following procedural changes necessitated by the incompatibility of structural features particular to this substrate and the typical synthetic methodology. Upon formation of the initial (trimethyl)silylmethyllithium addition adduct to enone 13, the phenolic protecting group was exchanged prior to effecting elimination, using the following protocol adhered to for all cyclocymopol analogs incorporating the methylidene olefin into a 1,3-diene moiety. The crude addition product (0.090 g, 0.166 mmol) was dissolved in 5 mL anhydrous THF containing 0.20 mL acetic anhydride (large excess), and cooled to 0° C. under nitrogen atmosphere. Tetra-(n-butyl)ammonium fluoride (0.20 mL of a 1.0 M solution in THF, 0.20 mmol, 1.20 equiv) was added, and the mixture was allowed to warm to room temperature. The contents of the flask were then poured into a separatory funnel containing 30 mL ethyl acetate and 10 mL 1.0M $NaHSO_4$, the layers were separated, and the organic phase was washed with 10 mL brine, dried over $Na_2SO_4$, and concentrated under diminished pressure. The crude material thus obtained was immediately carried on to the next step by transferring to a 10 mL Nalgene vial containing 2–3 mL THF, and 0.3 mL premade HF/pyridine complex was added. After stirring overnight at room temperature, the reaction mixture was worked up in the usual manner, and purification by flash column chromatography (silica gel, hexanes/ethyl acetate, gradient elution) afforded 38.3 mg (64%) of the desired acetoxy-diene as a colorless, oily solid. $^1$H NMR (400 MHz, $CDCl_3$) $\delta$0.73 and 1.11 (2s, 2×3H, geminal-$CH_3$'s), 2.27 (s, 3H, acetate-$CH_3$), 3.83 (s, 3H, $OCH_3$), 4.13 and 4.68 (2s, 2×1H, methylidene-$CH_2$), 5.70 and 6.04 (2dd, 2×1H, 2-H, 3-H), 6.52 (s, 1H, 6'-H), 7.19 ppm (s, 1H, 3'-H). [Compound 17 is referred to as COMPOUND "F" or 102032]

1-Methylidene-6-(2'-hydroxy-4'-bromo-5'-methoxyphenyl)methyl-5,5-dimethylcyclo-hex-2-ene (18):

In a 10 mL test tube was combined 1-methylidene-6-(2'-acetoxy-4'-bromo-5'-methoxyphenyl)methyl-5,5-dimethylcyclohexene (17) (10.0 mg, 0.026 mmol) and 2.0 mL of 5% methanolic $K_2CO_3$. After 10 rain at room temperature, the methanol was removed by rotary evaporation, and the resultant residue was dissolved in 20 mL ethyl acetate. The organic solution was then washed with saturated aqueous $NH_4Cl$, dried over $Na_2SO_4$, and concentrated under diminished pressure. Purification by flash column chromatography (silica gel deactivated with triethylamine, hexanes / ethyl acetate, gradient elution) afforded 7.1 mg (81%) of the phenolic diene as a colorless, oily solid. $^1$H NMR (400 MHz, $CDCl_3$) $\delta$0.73 and 1.16 (2s, 2×3H, geminal-$CH_3$'s), 3.82 (s, 3H, $OCH_3$), 4.23 and 4.72 (2s, 2×1H, methylidene-$CH_2$), 5.78 and 6.08 (2dd, 2×1H, 2-H, 3-H), 6.51 (s, 1H, 6'-H), 6.99 ppm (s, 1H, 3'-H). [Compound 18 is hereinafter also referred to as COMPOUND "W" or 120033]

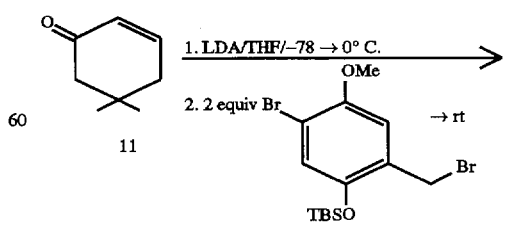

-continued

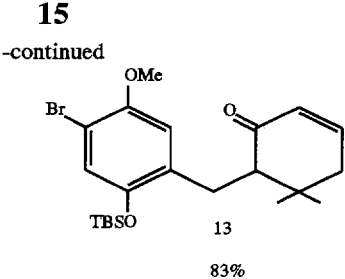

83%

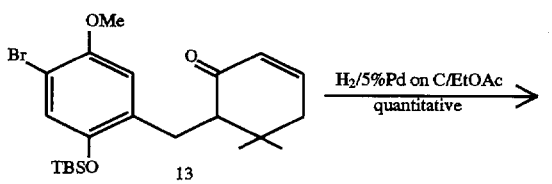

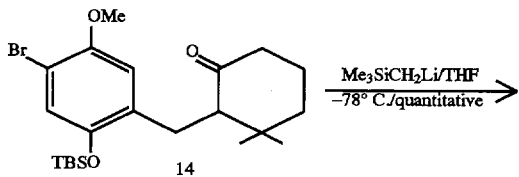

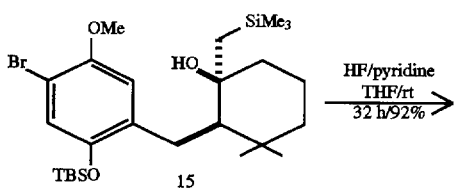

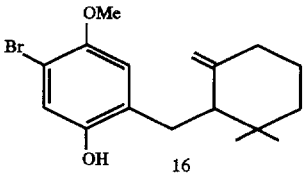

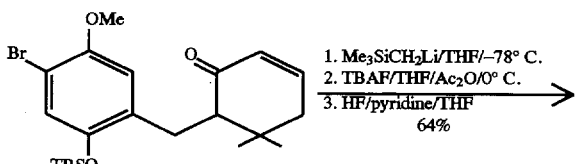

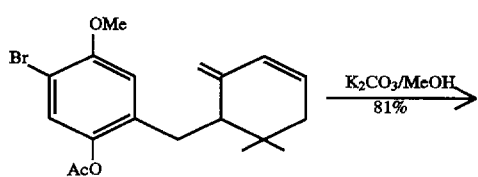

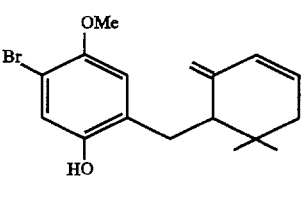

EXAMPLE 6

6-[2'(tert-Butyl)dimethylsilyloxy-4-bromo-5'methoxyphenyl]methyl-3,5,5-trimethyl-cyclohex-2-en-1-one (19):

This compound was prepared from isophorone (0.168 g, 1.22 mmol) in the manner previously described for enone 13, affording 0.342 g (60%) of the alkylation product (Rf 0.40, 2:1 hexanes/ethyl acetate) as a colorless, oily solid. $^1$H NMR (400 MHz, CDCl$_3$) δ0.20 and 0.22 [2s, 2×3H, Si(CH$_3$)$_2$], 0.99 [s, 9H, SiC(CH$_3$)$_3$], 1.00 and 1.02 (2s, 2×3H, geminal-CH$_3$'s),b 1.91 (s, 3H, 3-CH$_3$), 2.18 and 2.28 (ABq, 2H), 2.42 (dd, 1H), 2.82 (dd, 2H), 3.70 (s, 3H, OCH$_3$), 5.82 (sl d, 1H, 2-H), 6.71 (s, 1H, 6'-H), 6.92 ppm (s, 1H, 3'-H).

1-Methylidene-6-(2'-acetoxy-4'-bromo-5'-methoxyphenyl)methyl-3,5,5-trimethylcyclohex-2-ene (20):

This compound was prepared from 6-[2'-(tert-butyl)dimethylsilyloxy-4'-bromo-5'-methoxyphenyl]methyl-3,5,5-trimethylcyclohex-2-en-1-one (19) (42.0 mg, 0.090 mmol) in the manner previously described for acetoxy diene 17, affording 18.4 mg (52%) of the acetoxy-diene as a colorless oil. 1H NMR (400 MHz, CDCl$_3$) a 0.87 and 1.11 (2s, 2×3H, geminal-CH$_3$'s). 1.78 (s, 3H, 3-CH$_3$), 2.26 (s, 3H, acetate-CH$_3$), 3.83 (s, 3H, OCH$_3$), 4.03 and 4.58 (2s, 2×1H, methylidene-CH$_2$), 5.82 (s, 1H, 2-H), 6.52 (s, 1H, 6'-H), 7.19 ppm (s, 1H, 3'-H).

8-(2'-Acetoxy-4'-bromo-5'-methoxyphenyl)methyl-5,7,7-trimethylspiro[2.5]oct-4-ene (21):

To a flame-dried 10 mL round-bottomed flask containing 20.0 mg (0.051 mmol) 1-methylidene-6-(2'-acetoxy-4'-bromo-5'-methoxyphenyl)methyl-3,5,5-trimethylcyclohex-2-ene (20) in 1 mL 1,2-dichloroethane under nitrogen atmosphere at 0° C. was added diethylzinc (254 μL of a 1.0 M solution in hexanes, 0.255 mmol, 5.0 equiv). Chloroiodomethane (37 μL, 0.510 mmol, 10.0 equiv) was added dropwise, and the mixture was allowed to warm to room temperature. After 9 h, the reaction mixture was quenched at 0° C. with saturated aqueous NH$_4$C$_1$, and the reaction mixture was extracted with ethyl acetate (50 mL). The organic phase was washed with brine (20 mL), dried over Na$_2$SO$_4$, and concentrated under diminished pressure. Purification by flash column chromatography (silica gel, hexanes/ethyl acetate, gradient elution) afforded 20 mg (96%) of the spirocyclopropane as a colorless, viscous oil. $^1$H NMR (400 MHz, CDCl$_3$) δ−0.07 (ddd, 1H, J=11.0, 9.3, 5.9 Hz, cyclopropyl-H), 0.16 (ddd, 1H, J=11.5, 9.4, 6.1 Hz, cyclopropyl-H), 0.32 (ddd, 1H, J=10.1, 5.8, 5.8 Hz, cyclopropyl-H), 0.43 (ddd, 1H, J=9.8, 6.1, 6.1 Hz, cyclopropyl-H), 1.03 and 1.06 (2s, 2×3H, geminal-CH$_3$'s), 1.60 and 1.98 (ABq, 2H, J$_{AB}$=17.8 Hz, 6-H), 1.69 (s, 3H, 5-CH$_3$), 2.25 (s, 3H, acetate-CH$_3$), 2.39 and 2.65 (d of ABq, 2H, J$_{AB}$=13.6 Hz, J$_B$=10.0 Hz, J$_B$=3.4 Hz, benzylic-CH$_2$), 3.86 (s, 3H, OCH$_3$), 4.68 (s, 4 -H), 6.69 (s, 1H, 6'-H), 7.18 ppm (s, 1H, 3'-H). [Compound 21 is hereinafter also referred to as COMPOUND "H" or 120299]

EXAMPLE 7 cis-2-[(2'-tert-Butyl)dimethylsilyloxy-4'-bromo-5'-methoxyphenyl]methyl-3,3,5-trimethylcyclohexan-1-one (22):

To a suspension of copper(I) iodide (2 mg) in 1 mL of anhydrous ether at 0°C. was added methylmagnesium bromide (0.106 mL of a 3.0 M solution in ether, 0.319 mmol, 1.00 equiv). Then enone 13 (149 mg, 0.319 mmol) in 2 mL of anhydrous ether was added slowly to the stirring cuprate mixture at a temperature maintained below 5° C., and upon completion of the addition, the reaction mixture was stirred at 0° C. for 3 h before quenching with a 4:1 mixture of saturated aqueous $NH_4Cl/NH_4OH$. The resultant biphasic mixture was extracted with ether, dried over $Na_2SO_4$, and concentrated under diminished pressure. Purification by flash column chromatography (silica gel, hexanes/ethyl acetate, 9:1) afforded 36 mg (30%) of the desired conjugate addition product as a white solid. $^1H$ NMR (400 MHz, $CDCl_3$) δ0.22 (s, 6H, $Si(CH_3)_2$), 1.00 [m, 18H, 3,3,5-$CH_3$ and $SiC(CH_3)_3$], 1.50 (dd, 2H, J=15.1, 6.5 Hz, 4-Hz, 4-H), 2.02 (m, 1H, 5-H), 2.14 and 2.23 (ABq, 2H, $J_{AB}$=12.0 Hz, 6-H), 2.42 (dd, 1H, J=10.4, 6.4 Hz, 2-H), 2.88 and 2.89 (d of ABq, 2H, $J_{AB}$=12.0 Hz, $J_A$=10.4 Hz, $J_B$=6.3 Hz, benzylic-$CH_2$), 3.82 (s, 3H, $OCH_3$), 6.65 (s, 1H, 6'-H), 6.92 ppm (s, 1H, 3'-H).

cis-1Methylidene-2-(2'-hydroxy-4'-bromo-5'-methoxyphenyl)methyl-3,3,5-trimethyl-cyclohexane (23):

To a solution of cis-2-[(2'-tert-butyl)dimethylsilyloxy-4'-bromo-5'-methoxyphenyl]methyl-3,3,5-trimethylcyclohexan-1-one (22) (7.5 mg, 0.016 mmol, 1.0 equiv) in 1 mL of anhydrous THF at −78° C. was added (trimethyl)silylmethyllithium (66 µL of a 1.0 M solution in pentane, 0.066 mmol, 4.0 equiv) and the mixture was stirred for 20 min, at which time TLC. analysis indicated complete consumption of starting material, and the reaction was quenched at −78° C. with 1 mL of saturated aqueous $NH_4Cl$ solution. The resulting biphasic mixture was allowed to warm to room temperature and was extracted with ethyl acetate (30 mL), and the organic layer was dried over $Na_2SO_4$, and concentrated under diminished pressure. Purification by flash column chromatography (silica gel, hexanes/ethyl acetate, 4:1 ) afforded 7.3 mg (86%) of the desired tertiary alcohol intermediate as a colorless oil. Five milligrams of this intermediate were placed in a 10 mL Nalgene vial containing 1 mL of dry THF, 68 gL of HF/pyridine complex were added, and the mixture was allowed to stir at room temperature for 32 h, after which time the contents of the vial were transferred into a separatory funnel containing 3 mL of ethyl acetate and 1 mL of 1M aqueous $NaHSO_4$. The layers were separated, and the organic phase was washed with 1 mL of brine, dried over $Na_2SO_4$, and concentrated under diminished pressure. Purification by flash column chromatography (silica gel, hexanes/ethyl acetate, 9: 1) afforded 2.7 mg (81%) of the desired phenol as a colorless, viscous oil. $^1H$ NMR (400 MHz, $CDCl_3$) a 0.92 and 1.06 (2s, 2×3H, geminal-$CH_3$'s), 0.95 (d, 3H, J=8.0 Hz, 5-$CH_3$), 1.84 (m, 2H), 2.09 (m, 1H), 2.10 (dd, 1H, J=13.3, 4.2 Hz, 2-H), 2.58 and 2.81 (d of ABq, 2H, $J_{AB}$=13.6 Hz, $J_A$=11.2 Hz, $J_B$=3.7 Hz, benzylic-$CH_2$), 3.81 (s, 3H, $OCH_3$), 4.27 and 4.58 (2s, 2×1H, methylidene-$CH_2$), 4.42 (s, 1H, OH), 6.53 (s, 1H, 6'-H), 6.94 ppm (s, 1H, 3'-H). [Compound 23 is hereinafter also referred to as COMPOUND "S" or 120275]

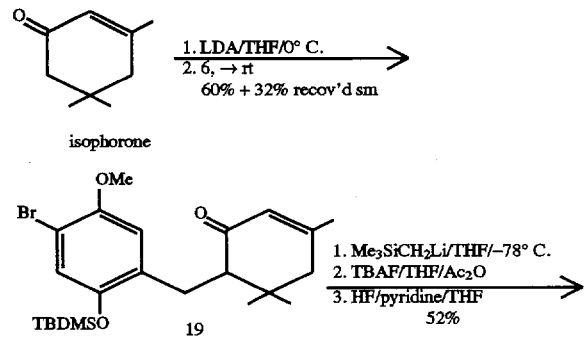

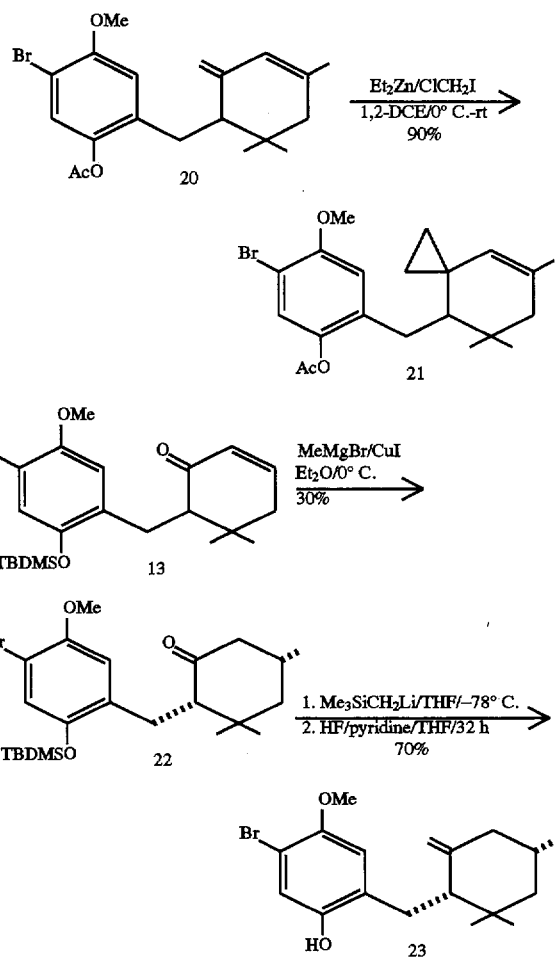

EXAMPLE 8

1-Methylidene-2-(2'-hydroxy-4'-bromo-5'methoxyphenyl)methyl-3,3-dimethylcyclo-pentane (26):

This compound was prepared from 4,4-dimethylcyclopent-2-en-1-one (24) and benzylic bromide 6 in 5 steps in the manner previously described for the synthesis of olefin 16, with the following procedural changes in the last two steps, from intermediate 25. To a flame-dried 25 mL round-bottomed flask containing a magnetic stir bar was added 340 mg (0.90 mmol) of cerium trichloride heptahydrate, and the flask was heated to 140° C. under vacuum for 2 h, after which time the solid was cooled to room temperature, and 3 mL of anhydrous THF was added. After stirring for 2 h at room temperature, the slurry was cooled to −78° C. and (trimethyl) silylmethyllithium (0.78 mL of a 1.0 M solution in pentane, 0.78 mmol) was added. After 30 min, 2-[(2tert-butyl)dimethylsilyloxy-4'-bromo-5'-methoxyphenyl]methyl-3,3-dimethylcyclopentanone 25 (15.0 mg, 0.034 mmol) in 1 mL of anhydrous THF was added, and the mixture was allowed to stir at −78° C. for 4 h, before quenching with saturated aqueous $NH_4C_1$. The reaction mixture was extracted with ether, and the organic phase was dried over $Na_2SO_4$, and concentrated under diminished pressure. Purification by flash column chromatography (silica gel, hexanes/ethyl acetate 9:1) gave 15 mg (83%) of the tertiary alcohol intermediate as a colorless oil. Compound 26 was prepared from this alcohol intermediate (7.3 mg, 0.014 mmol) in the manner previously described for the preparation of olefin 16, affording 3.0 mg (66%) of the desired product as a colorless oil. $^1$H NMR (400 MHz, CDCl$_3$) δ0.92 and 0.96 (2s, 2×3H, geminal-CH$_3$'s), 1.53 (m, 2H, 4-H), 2.39 (m, 3H, 2-H and 5-H), 2.57 and 2.67 (d of ABq, 2H, benzylic-CH$_2$), 3.81 (s, 3H, OCH$_3$), 4.50 (s, 1H, OH), 4.66 and 4.84 (2s, 2×1H, methylidene-CH$_2$), 6.74 (s, 1H, 6'-H), 6.99 ppm (s, 1H, 3'-H). [Compound 26 is hereinafter also referred to as COMPOUND "K" or 120192]

EXAMPLE 9

2-(2'-hydroxy-4'-bromo-5'-methoxyphenyl)methylcyclohex-1-one (28):

This compound was prepared in two steps from cyclohexanone and 2-(tert-butyl)dimethylsilyloxy-4-bromo-5-methoxybenzyl bromide (6) as previously described, to give the desired olefin in two steps in 50.4% overall yield as a colorless oil. 1H NMR (400 MHz, CDCl$_3$) δ2.49 (dd, 1H, 2H), 2.54 and 2.92 (d of ABq, 2H, benzylic-CH$_2$), 3.83 (s, 3H, OCH$_3$),4.46, (s, 1H, OH), 6.61 (s, 1H, 6'-H), 7.02 ppm (s, 1H, 3'-H). [Compound 28 is hereinafter also referred to as COMPOUND "Y" or 120125]

EXAMPLES 10-11

(5R, 6S)-6-[2'-(tert-Butyl)dimethysilyloxy-4'-bromo-5'-methoxyphenyl]methyl-5-methylcyclohex-2-en-1-one (29);

To a solution of lithium diisopropylamide (4.65 mL of a 2.0M solution in THF, 9.30 mmol, 2.2 equiv) in 15 mL of anhydrous THF and 4.4 mL of dry hexamethylphosphoramide (HMPA) at −35° C. was added dropwise ketosulfoxide 12 (prepared from (R)−(+)−pulegone according to the method of Oppolzer and Petrzika; Helv. Chim. Acta 1978, 61, 2755) in 5 mL of dry THF. The reaction mixture was stirred at −35° C. for 3 h, after which 2-(tert-butyl) dimethylsilyloxy-4-bromo-5-methoxybenzyl bromide (6) was added dropwise as a solution in 10 mL of anhydrous THF. The reaction mixture was allowed to stir for an additional 2 h at −35° C., quenched with 1M aqueous NaHSO$_4$ (15 mL) and extracted with ether (50 mL). The organic layer was washed with water (3×15mL) and brine (1×15 mL), then dried over Na$_2$SO$_4$ and concentrated under diminished pressure to afford 2.37g of the intermediate ketosulfoxide as a pale yellow oil, which was used directly in the next step without purification. A solution of the intermediate ketosulfoxide (2.37 g, 4.20 mmol) and CaCO$_3$ (0.40 g, 3.90 mmol) in 90 mL of carbon tetrachloride was brought to reflux for 3 h. Upon cooling to room temperature, the reaction mixture was filtered and the solvent was removed under diminished pressure. Purification by flash column chromatography (silica gel, hexanes/ethyl acetate, 95:5) afforded 550 mg (30%) of the desired enone. $^1$H NMR (400MHz, CDCl$_3$) δ0.18 and 0.22 [2s, 2×3H, Si(CH$_3$)$_2$], 1.03 [s, 9H, SiC(CH$_3$)$_3$], 1.05 (d, 3H, J=8.0 Hz, 5-CH$_3$), 2.07 (m, 2H), 2.50 (m, 1H, 6-H), 2.65 (m, 1H), 2.91 (m, 2H, benzylic-CH$_2$), 3.80 (s, 3H, OCH$_3$), 6.02 (d, 1H, J=9.4 Hz, 2-H), 6.70 (s, 1H, 6'-H), 6.85 (ddd, 1H, J=9.6, 4.1, 3.2 Hz, 3-H), 6.98 ppm (s, 1H, 3'-H).

(5R,6S)-1-Methylidene-6-(2'-acetoxy-4'-bromo-5'-methoxyphenyl)methyl-5-methylcyclohex-2-ene (30):

To a solution of (5R,6S)-6-[(2'-tert-butyl)dimethylsilyloxy-4'-bromo-5'-methoxyphenyl]methyl-5-methylcyclohex-2-en-1-one (29) (63 mg, 0.139 mmol, 1.00 equiv) in 2 ; mL of anhydrous THF at −78 ° C. was added (trimethyl)silylmethyllithium (222 μL of a 1.0M solution in pentane, 0.222 mmol, 1.60 equiv). After 10 minutes of stirring at −78 ° C., the reaction was quenched at −78° C. with 1 mL of saturated aqueous NH$_4$C$_1$. The reaction mixture was extracted with ethyl acetate, dried over Na$_2$SO$_4$ and concentrated under diminished pressure. Purification by flash column chromatography (silica gel, hexanes/ethyl acetate, 95:5) afforded 40.5 mg (60%) of the desired tertiary alcohol intermediate, along with 14 mg (22%) of unreacted starting material. This intermediate alcohol (14 mg, 0.028 mmol) was dissolved in 1 mL of anhydrous THF containing 60 mL (0.56 mmol, 20.0 equiv) of acetic anhydride, and cooled to 0° C. Tetra-(n-butyl)ammonium fluoride (33 μL of a 1.0M solution in THF, 0.033 mmol, 1.20 equiv) was added, and the mixture was allowed to warm to room temperature. The contents of the flask were then poured into a separatory funnel containing 5 mL of ethyl acetate and 2 mL of aqueous 1M NaHSO$_4$. The layers were separated, the organic phase was dried over Na$_2$SO$_4$, and the solvent was removed under diminished pressure. The crude intermediate (12.4 mg) was placed in a 10 mL Nalgene vial containing 2 mL of dry THF, 0.175 mL of premade HF/pyridine complex was added, and the mixture was allowed to stir at room temperature for 18 h. The contents of the vial were then transferred into a separatory funnel containing 5 mL of ethyl acetate and 3 mL of aqueous 1M NaHSO$_4$. The layers were separated, and the organic phase was washed with 2 mL of brine, dried over Na$_2$SO$_4$, and concentrated under diminished pressure. Purification by flash column chromatography (silica gel, hexanes lethyl acetate, 85:15) afforded 6.4 mg (60% for the 2 steps) of the desired acetylated phenol. $^1$H NMR (400MHz, CDCl$_3$) δ0.85 (d, 3H, 5-CH$_3$), 1.67 (m, 2H), 1.76 (s, 3H, 3-CH$_3$), 2.20 (dd, 1H). 2.27 (s, 3H, acetate-CH$_3$) CH$_3$), 2.49 (m, 3H), 3.86 (s, 3H, OCH$_3$), 4.40 and 4.71 (2s, 2×1H, methylidene-CH$_2$), 5.86 (s, 1H, 3-H), 6.64 (s, 1H, 6'-H), 7.21 ppm (s, 1H, 3'-H). [Compound 30 is hereinafter also referred to as COMPOUND "L" or 120260]

(5R$_6$S)-6-[2-(tert-Butyl)dimethylsilyloxy-4'-bromo-5'-methoxyphenyl]methyl-3,5-dimethylcyclohex-2-en-1-one (31):

To a suspension of copper(I) iodide (1.36 mg) in 0.5 mL of anhydrous ether at 0° C. was added methylmagnesium bromide (222 gL of a 3.0M solution in ether, 0.665 mmol, 1.00 equiv), causing the solution to turn dark. A solution of enone (29) (310 mg, 0.665 mmol) in 1 mL of anhydrous ether was the added over a period of 2 minutes keeping the temperature below 5° C. After the addition was complete, the mixture was stirred at 0° C. for an additional 30 minutes, at which time phenylselenenyl bromide (157 mg, 0.665 mmol) in 0.5 mL of anhydrous THF was added, keeping the temperature below 10° C. The resulting mixture was stirred for 10 minutes, poured into water (2 mL) and extracted with ether (5 mL). The organic phase was washed twice with water (2 mL), dried over Na$_2$SO$_4$ and concentrated under diminished pressure. The resultant oil was dissolved in 2 mL of dry dichloromethane and 162 μL of pyridine, and to this a solution of hydrogen peroxide 35% (181 μL) in 162 mL of water was added dropwise, keeping the temperature between 30°–35° C. and warming if necessary to initiate the reaction. The mixture was stirred at room temperature for 30 minutes, and then poured into a separatory funnel containing dichloromethane-saturated aqueous NaHCO$_3$. After extraction of the mixture with dichloromethane, the organic solution was washed successively with 10% aqueous HCl and brine, and dried over Na$_2$SO$_4$. The solvent was removed under diminished pressure, and the residue was purified by flash column chromatography (silica gel, hexanes/ethyl acetate, 9:1 ), affording 157 mg (60%) of the desired enone as a colorless oil. $^1$H NMR (400MHz, CDCl$_3$) δ5 0.15 and 0.20 [2s, 2×3H, Si(CH₃)₂], 0.97 [s, 9H, SiC(CH₃)₃], 0.95 (d, 3H, J=8.0 Hz, 5-CH₃), 1.90 (s, 3H, 3-CH₃), 1.95 (m, 2H), 2.38 (m, 1H), 2.59 (m, 1H, 6-H), 2.87 (m, 2H, benzylic-CH₂), 3.79 (s, 3H, OCH₃), 5.86 (s, 1H, 2-H), 6.69 (s, 1H, 6'-H), 6.96 ppm (s, 1H, 3'-H).

(5R,6S)-1-Methylidene-6-(2'-acetoxy-4'-bromo-5'-methoxyphenyl)methyl-3,5-dimethyl-cyclohex-2-ene (32);

To a solution of (5R,6S)-6-[2'-(tert-butyl)dimethylsilyloxy-4'-bromo-5'-methoxyphenyl)methyl-3,5-dimethylcyclohex-2-en-1-one (31) (63 mg, 0.139 mmol, 1.0 equiv) in 2 mL of anhydrous THF at −78° C. was added (trimethyl)silylmethyllithium (222 μL of a 1.0M solution in pentane, 0.222 mmol, 1.60 equiv). After 10 minutes of stirring at −78° C., the reaction was quenched at −78 ° C. with 1 mL of saturated aqueous NH₄Cl. The reaction mixture was extracted with ethyl acetate, dried over Na₂SO₄, and the solvent was removed under diminished pressure. Purification by flash column chromatography (silica gel, hexanes/ethyl acetate, 95:5), afforded 40.5 mg (60%) of the desired tertiary alcohol intermediate, along with 14 mg (22%) of unreacted starting material. This intermediate alcohol (14 mg, 0.028 mmol) was dissolved in 1 mL of anhydrous THF containing 60 μL (0.56 mmol, 20.0 equiv) of acetic anhydride and cooled to 0° C. Tetra-(n-butyl)ammonium fluoride (33 μL of a 1.0M solution in THF, 0.033 mmol, 1.2 equiv) was added, and the mixture was allowed to warm to room temperature. The contents of the flask were poured into a separatory funnel containing 5 mL of ethyl acetate and 2 mL of aqueous 1M NaHSO₄. The layers were separated, and the organic phase was dried over Na₂SO₄. The solvent was removed under diminished pressure, and the crude intermediate (12.4 mg) was placed in a 10 mL Nalgene vial containing 2 mL of dry THF, 0.175 mL of HF/pyridine complex was added, and the mixture was allowed to stir at room temperature for 18 h. The contents of the vial were transferred to a separatory funnel containing 5 mL of ethyl acetate and 3 mL of 1M aqueous NaHSO₄, the layers were separated, and the organic phase was washed with 2 mL of brine, dried over Na₂SO₄, and the solvent was removed under diminished pressure. Purification by flash column chromatography (silica gel, hexanes/ethyl acetate, 85:15) afforded 6.4 mg (60% for 2 steps) of the desired acetylated phenol as a colorless oil. ¹H NMR (400MHz, CDCl₃) δ0.85 (d, 3H, 5-CH₃), 1.67 (m, 2H), 1.76 (s, 3H, 3-CH₃), 2.27 (s, 3H, acetate-CH₃), 2.49 (m, 3H), 3.86 (s, 3H, OCH₃), 4.40 and 4.71 (2s, 2×1H, methylidene-CH₂), 5.86 (s, 1H, 3-H), 6.64 (s, 1H, 6'-H), 7.21 ppm (s, 1H, 3'-H). [Compound 32 is hereinafter also referred to as COMPOUND "O" or 120276]

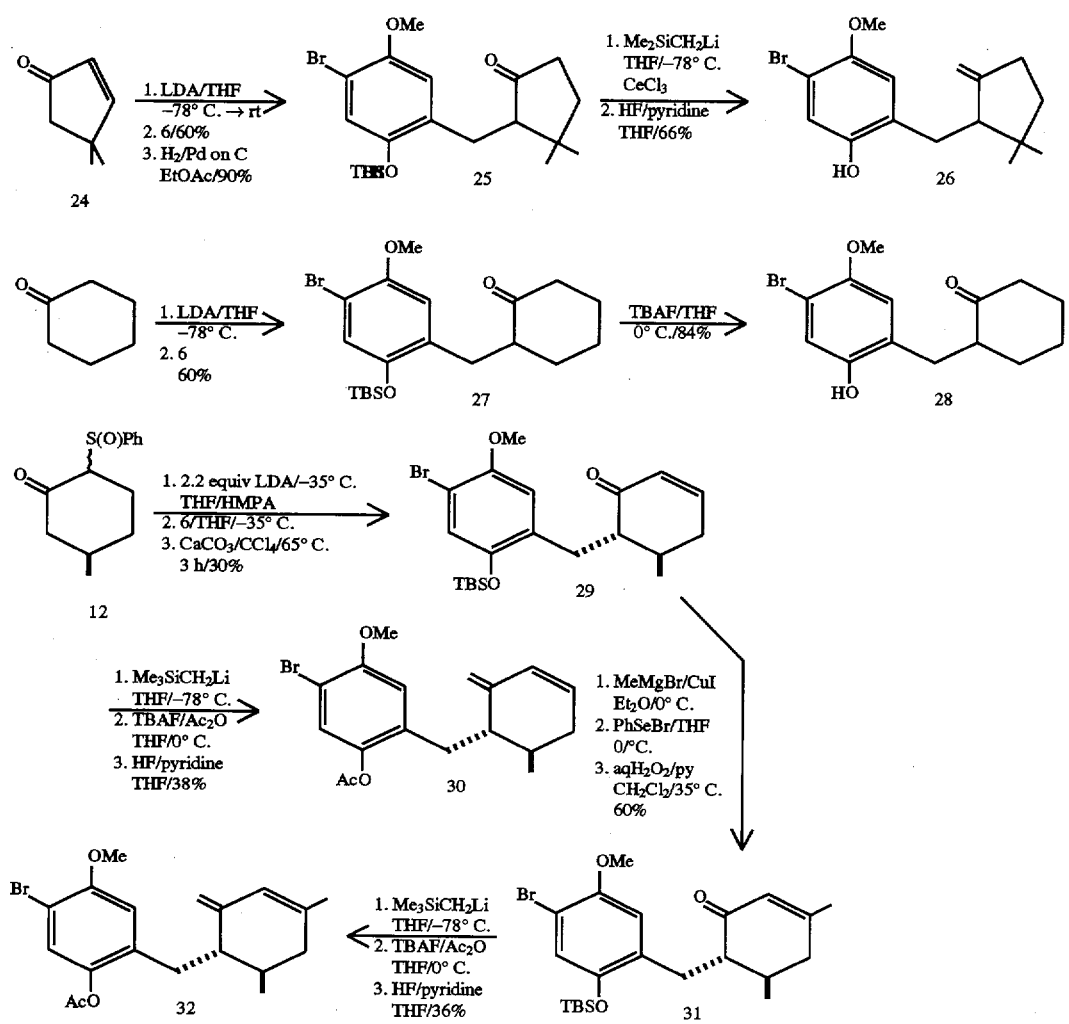

5,677,336

EXAMPLE 12

1-Methylidene-6-(2'-hydroxyphenyl)methyl-5,5-dimethylcyclohex-2-ene (34):

This compound was prepared from 5,5-dimethylcyclohex-2-en-1-one (11) and 2-(tert-butyl)dimethylsilyloxybenzyl bromide (9) in three steps in the manner previously described for the synthesis of olefin 16, affording the desired phenol as a colorless oil. $^1$H NMR (400MHz, CDCl$_3$) δ0.90 and 1.15 (2s, 2×3H, geminal-CH$_3$'s), 1.85 and 2.24 (d of ABq, 2H, J$_{AB}$=18.8 Hz, J$_A$=5.5 Hz, J$_B$=0 Hz, 4-H), 2.06 (dd, 1H, J=11.4, 3.2 Hz, 6-H), 3.30 and 2.88 (d of ABq, 2H, J$_{AB}$=13.5 Hz, J$_A$=11.4 Hz, J$_B$=3.4 Hz, benzylic-CH$_2$), 4.20 and 4.69 (2s, 2×1H, methylidene-CH$_2$), 4.61 (s, 1H, OH), 5.77 (ddd, 1H, J=7.8, 5.4, 5.4 Hz, 3-H), 6.09 (dd, 1H, J=7.5, 2.2 Hz, 2-H), 6.75 (dd, 1H, J=7.1, 0.8 Hz, 3'-H), 6.82 (ddd, 1H, J=8.4, 7.3, 1.1 Hz, 5'-H), 6.97 (dd, 1H, J=5.9, 1.5 Hz, 6'-H), 7.05 ppm (ddd, 1H, J=9.3, 7.8, 1.7 Hz, 4'H). [Compound 34 is hereinafter also referred to as COMPOUND "C" or 120363]

EXAMPLE 13

1-Methylidene-2-(2'-hydroxyphenyl)methyl-5,5-dimethylcyclohexane (35):

This compound was prepared from 5,5-dimethylcyclohex-2-en-1-one (11) and 2-(tert-butyl)dimethylsilyloxybenzyl bromide (9) in four steps in the manner previously described for the synthesis of olefin 16, affording the desired olefin as a colorless oil. $^1$H NMR (400MHz, CDCl$_3$) δ0.97 and 1.01 (2s, 2×3H, geminal-CH$_3$'s), 2.09 (ddd, 1H) and 2.27 (ddd, 1-H) [6-H], 2.18 (dd, 1H, 2-H), 2.70 and 2.84 (d of ABq, 2H, benzylic-CH$_2$), 4.37 (sl d, 1H) and 4.63 (s, 1H) [methylidene-CH$_2$], 4.72 (s, 1H, OH), 6.72 (d, 1H, 3'-H), 6.81 (dd, 1H, 5'-H), 7.03 (d, 1H, 6-H), 7.04 ppm (dd, 1H, 4'-H). [Compound 35 is hereinafter referred to as COMPOUND "D" or 120370]

EXAMPLE 14 trans-1-Methyl-2-(2'-hydroxy-4'-bromo-5'-methoxyphenyl)methylcyclohexan-1-ol (36):

To a solution of 2-[(2'-tert-butyl)dimethylsilyloxy-4'-bromo-5'-methoxyphenyl]methylcyclohexan-1-one (27) (10 mg, 0.023 mmol) in 1 mL of anhydrous ether at −78° C. was added methylmagnesium bromide (8.0 µL of a 3.0M solution in ether, 0.024 mmol, 1.06 equiv). The reaction mixture was stirred at −78° C. for 30 minutes and quenched with saturated aqueous NH$_4$C$_1$, extracted with ether, and the organic phase was dried over Na$_2$SO$_4$ and concentrated under diminished pressure. Purification by flash column chromatography (silica gel, hexanes/ethyl acetate, 4:1) gave 10 mg (97%) of the desired tertiary alcohol as a colorless oil. To a solution of 10 mg (0.021 mmol) of this tertiary alcohol in 1 mL of dry THF at 0° C. was added tetra-(n-butyl)ammonium fluoride (25 µL of a 1.0M solution in THF, 0.025 mmol, 1.2 equiv), and the reaction mixture was allowed to stir for 20 minutes, then diluted with water, and extracted with ethyl acetate. The organic phase was washed with brine, dried over Na$_2$SO$_4$ and concentrated under diminished pressure. Purification by flash column chromatography (silica gel, hexanes/ethyl acetate, 4:1) gave 6 mg (80%) of the desired tertiary alcohol as a colorless, viscous oil. $^1$H NMR (400MHz, CDCl$_3$) δ1.32 (s, 3H, CH$_3$), 2.45 and 2.93 (d of ABq, 2H, benzylic-CH$_2$), 3.83 (s, 3H, OCH$_3$), 6.61 (s, 1H, 6'-H), 7.04 ppm (s, 1H, 3'-H). [Compound 36 is hereinafter also referred to as COMPOUND "Q" or 120136]

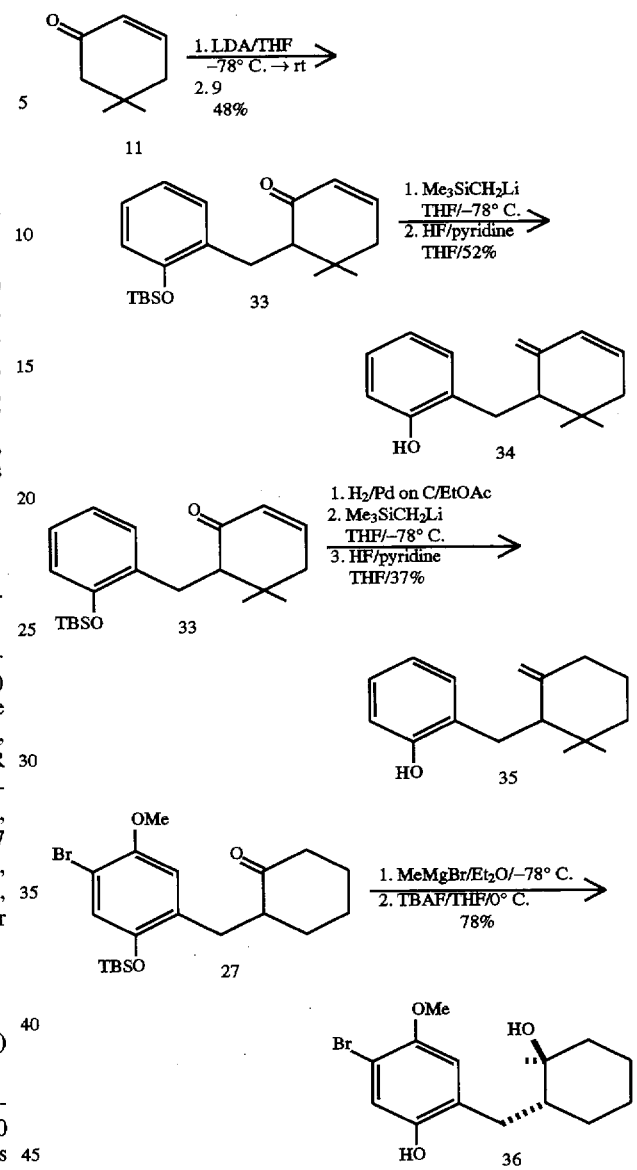

EXAMPLE 15

1-Methylidene-6-(3'-nitrophenyl)methyl-5,5-dimethylcyclohex-2-ene (38):

This compound was prepared from 5,5-dimethylcyclohex-2-en-1-one (11) (0.150 g, 1.21 mmol) and m-nitrobenzyl bromide (0.510 g, 2.42 mmol, 2.00 equiv) in three steps in the manner previously described for the synthesis of olefin 16, affording 42.7 mg (26% overall), of the nitro-diene as a pale yellow oil. $^1$H NMR (400MHz, CDCl$_3$) δ0.91 and 1.13 (2s, 2×3H, geminal-CH$_3$'s), 1.99 and 2.12 (d of ABq, 2H, benzylic-CH$_2$), 4.07 and 4.89 (2s, 2×1H, methylidene-CH$_2$), 5.77 and 6.00 (2dd, 2×1H, 2,3-H), 7.42 (dd, 1H, Ar—H), 7.59 (d, 1H, Ar—H), 7.96 (d, 1H, Ar—H), 8.00 ppm (s, 1H, Ar—H). [Compound 38 is hereinafter also referred to as COMPOUND "A" or 120117]

EXAMPLE 16

6-(4'-Nitrophenyl)methyl-5,5-dimethylcyclohex-2-en-1-one (39):

This compound was prepared from 5,5-dimethylcyclohex-2-en-1-one (11) (0.600 g, 4.83 mmol) and p-nitrobenzyl bromide (1.581 g, 7.32 mmol) in the manner previously described for the synthesis of enone 13, affording 627 mg (50%), of the nitro-enone as a pale yellow oil. 1H NMR (400MHz, CDCl$_3$) δ1.02 and 1.18 (2s, 2×3H, geminal-CH$_3$'s), 2.83 and 3.10 (d of ABq, 2H, benzylic-CH$_2$), 6.00 (ddd, 1H, 2-H), 6.81 (ddd, 1H, 3-H), 7.38 and 8.10 ppm (ABq, 2×2H, Ar—H).

2-(4'-Nitrophenyl)methyl-3,3-dimethylcyclohexan-1-one (40):

An atmosphere of hydrogen was introduced to and maintained by a balloon to an evacuated 50 mL round-bottomed flask containing 6-(4'-nitrophenyl)methyl-5,5-dimethylcyclohex-2-en-1-one (39) (14.0 mg, mmol) and tris(triphenylphosphine)rhodium chloride (Wilkinson's catalyst) (8.0 mg) in 6.5 mL anhydrous benzene. The yellow-orange solution was stirred at room temperature for 24 h, and then passed through a short silica gel column (hexanes/ethyl acetate, 3:1) to afford the 6.8 mg (48%) of the desired ketone as a pale yellow oil (Rf0.43, 2:1 hexanes lethyl acetate). $^1$H NMR (400MHz, CDCl$_3$) δ0.86 and 1.23 (2s, 2×3H, geminal-CH$_3$'s), 2.50 (d, 1H, J=13.0 Hz, 2-H), 2.66 and 3.17 (d of ABq, 2H, J$_{AB}$=13.0 Hz, J$_A$=1.6 Hz, J$_B$=9.6 Hz, benzylic-CH$_2$), 7.37 (d, 2H, J=9.6 Hz, 2', 6'-H), 8.09 ppm (d, 2H, J=9.6 Hz, 3',5'-H). [Compound 40 is hereinafter also referred to as COMPOUND "V" or 120211]

EXAMPLE 17

1-Methylidene-6-(3'-methyl-4'-nitrophenyl)methyl-5,5-dimethylcyclohex-2-ene (41):

This compound was prepared from 6-(4'-nitrophenyl)methyl-5,5-dimethylcyclohex-2-en-1-one (39) (133 mg, 0.514 mmol) in the manner previously described for the synthesis of olefin 16, with the following procedural changes. Three equivalents of (trimethyl)silylmethyllithium were used, and the subsequent elimination step required 48 h to go to completion, affording 120 mg (86%) of the nitro-diene as a colorless oil. 1H NMR (400MHz, CDCl$_3$) δ0.92 and 1.12 (2s, 2×3H, geminal-CH$_3$'s), 2.58 (s, 3H, Ar—Ch$_3$), 4.05 and 4.64 (2s, 2×1H, methylidene-CH$_2$), 5.70 (ddd, 1H, 3-H), 6.03 (dd, 1H, 2-H), 6.98 (s, 1H, Ar—H), 6.99 and 7.88 ppm (2d, 2×1H, Ar—H). [Compound 41 is hereinafter also referred to as COMPOUND "T" or 120120]

EXAMPLE 18

6-(4'-Nitrophenyl)methyl-3,5,5-trimethylcyclohex-2-en-1-one (42):

This compound was prepared from isophorone (2.065 g, 14.94 mmol) and p-nitrobenzyl bromide (4.06 g, 18.80 mmol, 1.25 equiv) in the manner previously described for the synthesis of enone 13, affording 1.891 g (46%), of the nitro-enone as a pale yellow oil. $^1$H NMR (400MHz, CDCl$_3$) δ0.98 and 1.13 (2s, 2×3H, geminal-CH$_3$'s), 1.92 (s, 3H, 3-CH$_3$), 2.17 and 2.31 (ABq, 2H, J$_{AB}$=18.5 Hz, 4-H), 2.38 (dd, 1H, J=9.0, 3.3 Hz, 6-H), 2.75 and 3.05 (d of ABq, 2H, J$_{AB}$=14.0 Hz, J$_A$=3.2 Hz, J$_B$=8.9 Hz, benzylic-CH$_2$), 5.84 (s, 1H), 7.33 (d, 2H, J=8.2 Hz, Ar—H) and 7.53 ppm (d, 2H, J=8.2 Hz, Ar—H).

1-Methylidene-6-(3'-methyl-4'-nitrophenyl)methyl-3,5,5-trimethylcyclohex-2-ene (43):

This compound was prepared from 6-(4'-nitrophenyl)methyl-3,5,5-trimethylcyclohex-2-en-1-one (42) (21.0 mg, 0.077 mmol) in the manner previously described for the synthesis of olefin 16, using three equivalents of (trimethyl)silylmethyllithium, and allowing 18 h for the subsequent elimination step, affording 3.5 mg (16%) of the nitro-diene as a pale yellow oil. $^1$H NMR (400MHz, CDCl$_3$) δ0.89 and 1.15 (2s, 2×3H, geminal-CH$_3$'s), 1.96 and 2.10 (ABq, 2H, benzylic-CH$_2$), 2.58 (s, 3H, Ar—Ch$_3$), 2.92 (dd, 1H, 6-H), 3.96 and 4.54 (2s, 2×1H, methylidene-CH$_2$), 5.82 (s, 1H, 2-H), 6.98 (s, 1H, Ar—H), 6.99 and 7.88 ppm (2d, 2×1H, Ar—H). [Compound 43 is hereinafter also referred to as COMPOUND "U" or 120168]

EXAMPLES 19–20

2-(4'-Nitrophenyl)methylcyclohexan-1-one (44):

To a solution of diisopropylamine (342 μL, 2.45 mmol, 1.2 equiv) in 5 mL of anhydrous THF at 0° C. was added n-butyllithium (1.63 mL of a 1.6M solution in hexane), and the mixture was stirred at this temperature for 15 minutes before cooling to −78 ° C. Cyclohexanone (221 μL, 2.04 mmol, 1.0 equiv) in 2 mL of anhydrous THF was then added dropwise, stirred at −78 ° C. for 1 h followed by p-nitrobenzyl bromide (880 me, 4.08 mmol, 2.00 equiv) in 2 mL of THF, added dropwise to the resulting enolate. The reaction mixture was stirred at room temperature for 17 h, and then quenched with aqueous saturated NH$_4$C$_1$, and extracted with ether. The organic phase was dried over Na$_2$SO$_4$ and concentrated under diminished pressure to a solid residue that was purified by flash chromatography (silica gel, hexanes/ethyl acetate, 85:15), which afforded 300 mg (64%) of the desired ketone as a yellow solid. 1H NMR (400MHz, CDCl$_3$) δ1.41 (m, 1H), 1.66 (m, 2H), 1.88 (m, 1H), 2.08 (m, 2H), 2.33 (m,, 1H), 2.45 (m, 1H), 2.57 (m, 1H, 2-H), 2.59 and 3.29 (d of ABq, 2H, benzylic-CH$_2$), 7.34 (d, 2H, Ar—H), 8.12 ppm (d, 2H, Ar—H). [Compound 44 is hereinafter also referred to as COMPOUND "G" or 1201381]

trans-2-(4'-Nitrophenyl)methylcyclohexan-1-ol (45):

To a stirring solution of 2-(4'-nitrobenzene)methylcyclohexan-1-one (44) in 5 mL of methanol at 0° C. was added portionwise sodium borohydride, and the reaction mixture was allowed to stir at 0° C. for 1.5 h before quenching with saturated aqueous NH$_4$C$_1$. The methanol was removed under diminished pressure, and the resultant aqueous residue was extracted with ethyl acetate. The organic phase was washed with brine, dried over Na$_2$SO$_4$, and concentrated under diminshed pressure. Purification by flash column chromatography (silica gel, hexanes/ethyl acetate, 4:1) gave 10 mg (20%) of the desired alcohol 45, along with 18 mg (36%) of the diastereoisomeric alcohol 46 as colorless oils. Data for alcohol 45:1H NMR (400MHz, CDCl$_3$) δ0.92 (m, 1H), 1.11 (m, 1H), 1.28 (m, 3H), 1.60 (m, 2H), 1.76 (m, 1H), 2.02 (m, 1H, 2-H), 2.51 and 3.59 (d of ABq, 2H, benzylic-CH$_2$), 3.27 (m, 1H, 1-H), 7.34 (d, 2H, Ar—H), 8.15 ppm (d, 2H, Ar—H). [Compound 45 is hereinafter also referred to as COMPOUND "T" or 120154]

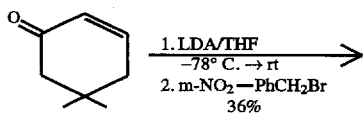

11

-continued

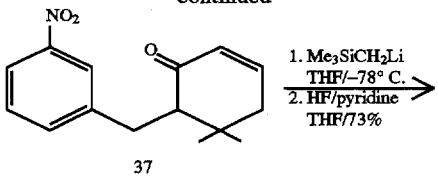

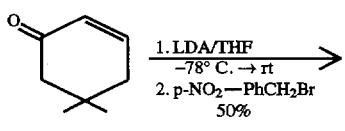

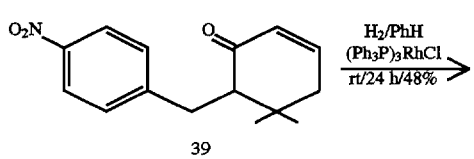

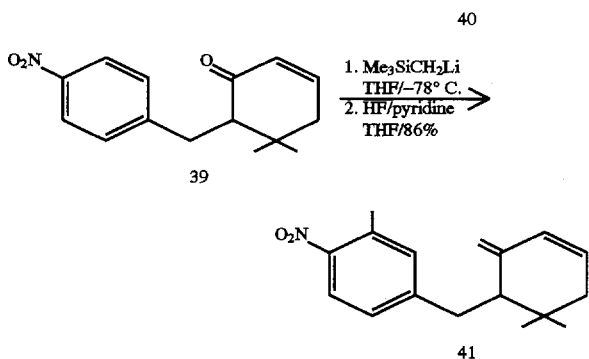

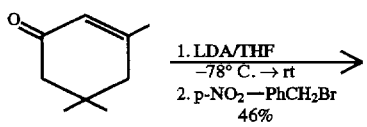

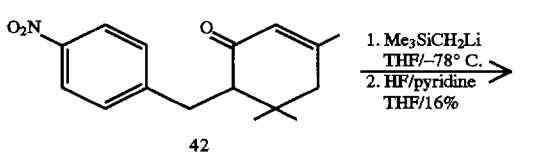

-continued

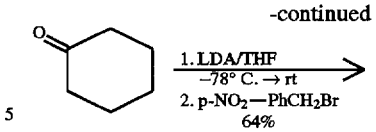

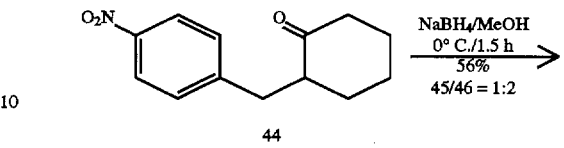

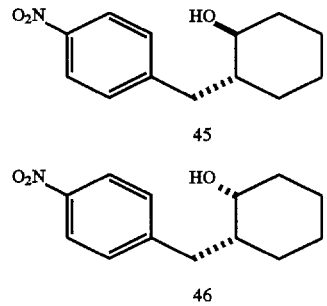

EXAMPLE 21

(2R)-1-Methylidene-2-(2'-hydroxy-4'-bromo-5'-methoxyphenyl)methyl-3,3-dimethyl-cyclohexane (49):

To a flame-dried 10 mL round-bottomed flask containing (1S,3R)-4-methylidene-1-bromo-3-[2'(tert-butyl)dimethylsilyloxy-4'-bromo-5 '-methoxyphenyl]methyl-2,2-dimethyl-cyclohexane (47) (19.5 mg, 0.036 mmol) in 1 mL anhydrous benzene with 2 mg AIBN at room temperature was added n-Bu₃SnH (39 μL, 0.144 mmol, 4.0 equiv). After 90 min, TLC analysis indicated virtually complete consumption of starting material, and formation of a slightly less polar product. Carbon tetrachloride (200 μL) was added, and after 1 h at room temperature followed by 1.5 h at 0° C., 2 mL THF and 200 μL 1.0M tetra-(n-butyl)ammonium fluoride solution in THF were added. After 10 min at 0° C., pH 7 buffer was added, and the reaction mixture was extracted with hexanes. The resultant organic solution was dried over Na₂SO₄, and concentrated under diminished pressure. Purification by flash column chromatography (silica gel, 10% ethyl acetate in hexanes) afforded 7.5 mg (61%) of the debromophenol as a colorless oil. The 400MHz ¹H NMR spectrum and TLC. elution properties of this compound were identical to those reported for the racemic compound. [Compound 49 is hereinafter also referred to as COMPOUND "N" or 120037]

EXAMPLE 22

(2S)-1-Methylidene-2-(2'-hydroxy-4'-bromo-5'-methoxyphenyl)methyl-3,3-dimethyl-cyclohexane (52):

This compound was prepared from (1S,3S)-4-methylidene-1-bromo-3-[2'-(tert-butyl)dimethylsilyloxy-4'-bromo-5'-methoxyphenyl]methyl-2,2-dimethylcyclohexane (50) (25.0 mg, 0,047 mmol) in the manner described for the synthesis of derivative 49, affording 5,5 mg (35%) of the debromophenol as a colorless oil, along with the remainder of the mass balance as deprotected starting material. The 400MHz 1H NMR spectrum and TLC. elution properties of this compound were identical to those reported for the racemic compound. [Compound 52 is hereinafter also referred to as COMPOUND "X" or 120158]

EXAMPLE 23

(1S,3S,5S)-4-Methylidene-1-1-bromo-5-hydroxy-3-(2'-acetoxy-4'-bromo-5'-methyoxyphenyl)methyl-2,2-dimethylcyclohexane (54):

To a flame-dried 25 mL round-bottomed flask containing (1S,3S)-4-methylidene-1-bromo-3-(2'-acetoxy-4'-bromo-5'-methyoxyphenyl)methyl-2,2-dimethylcyclohexane (53) (22.8 mg, 0.050 mmol) in 2.5 mL anhydrous dichloromethane at room temperature was added selenium dioxide (5.5 mg, 0.050 mmol, 1.00 equiv) and anhydrous t-butyl hydroperoxide (60 μL of a 3.0M solution in 2,2,4-trimethylpentane, 1.00 mmol, 2.00 equiv), and the mixture was allowed to stir at room temperature for 48 h, at which time the solvent was removed by rotary evaporation. Purification by flash column chromatography (silica gel, hexanes/ethyl acetate, gradient elution) afforded 20 mg (84%) of the hydroxycyclocymopol acetate as a white solid. 1H NMR (400 MHz, CDCl$_3$) δ0.94 and 1.24 (2s, 2×3H, geminal-CH$_3$'s), 2.23 and 2.41 (dd of ABq, 2H, J$_{AB}$=14.0 Hz, J$_A$=11.7, 3.5 Hz, J$_B$=4.2, 4.2 Hz, 6-H), 2.32 (s, 3H, acetate-CH$_3$), 2.73 and 2.86 (dd of ABq, 2H, J$_{AB}$=15.2 Hz, J$_A$=11.3, 0.5 Hz, J$_B$=15.3, 3.0 Hz, benzylic-CH$_2$), 3.84 (s, 3H, OCH$_3$), 4.31 (br s, 1H, 1-H), 4.55 (dd, 1H, J=11.7, 4.4 Hz, 5-H), 4.69 and 5.03 (2s, 2×1H, methylidene-CH$_2$), 6.75 (s, 1H, 6'-H), 7.19 ppm (s, 1H, 3'-H).

(4S,6S)-1-Methylidene-4-bromo-5-(2'-acetoxy-4'-bromo-5'-methyoxyphenyl)methyl-5,5-dimethylcyclohex-2-ene (55):

To a flame-dried 10 mL round-bottomed flask containing (1S,3S,5S)-4-methylidene-1-bromo-5-hydroxy-3-(2'-acetoxy-4'-bromo-5'-methyoxyphenyl)methyl-2,2-dimethylcyclohexane (54) (6.8 mg, 0.014 mmol) in 2 mL anhydrous benzene at room temperature was added Burgess reagent [(methoxycarbonylsulfamoyl)triethylammonium hydroxide, inner salt](8.5 mg, 0.036 mmol, 2.5 equiv), and the mixture was allowed to stir for 12 h. Removal of the solvent under diminished pressure, followed by purification by flash column chromatography (silica gel, hexanes/ethyl acetate, gradient elution) afforded 4.8 mg (74%) of the desired diene as a colorless oil. $^1$H NMR (400MHz, CDCl$_3$) δ0.94 and 1.18 (2s, 2×3H, geminal-CH$_3$'s), 2.33 (s, 3H, acetate-CH$_3$), 3.78 (s, 3H, OCH$_3$), 4.69 and 4.78 (2s, 2×1H, methylidene-CH$_2$), 5.44 and 5.50 (2dd, 2×1H, 5,6-H), 6.64 (s, 1H, 6'-H), 7.00 ppm (s, 1H, 3'-H). [Compound 55 is hereinafter also referred to as COMPOUND "E" or 120261]

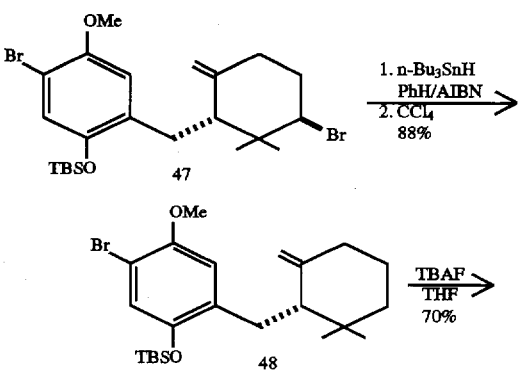

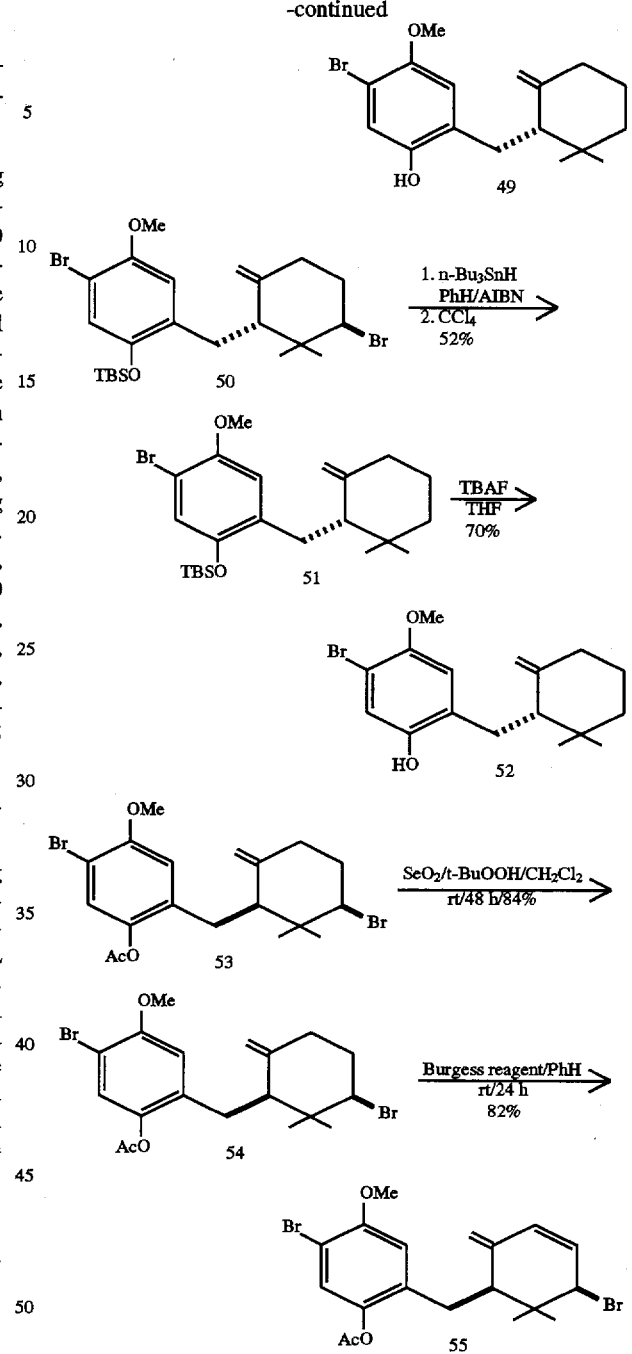

EXAMPLE 24

(1R,3R)-1-Hydroxy-2-methylidene-3-(2'-hydroxy-4'-bromo-5'-methoxyphenyl)methyl-4,4-dimethylcyclohexane (56) and (1S,3R)-1-Hydroxy-2-methylidene-3-(2'-hydroxy-4'-bromo-5'-methoxyphenyl)methyl-4,4-dimethylcyclohexane (57):

This set of diastereomeric alcohols was prepared from (2R)-1-methylidene-2-[2'-(tert-butyl)dimethylsilyloxy-4'-bromo-5'-methoxyphenyl]methyl-3,3-dimethylcyclohexane (48) (0.750 g, 1.66 mmol) in the manner previously described for the synthesis of alcohol 54, affording 741 mg (95%) of an inseparable 1:1 mixture of diastereomeric allylic alcohols. A portion (40 mg, 0.085 mmol) of this diastereomeric mixture was subjected to deprotection of the silylphenol in the usual manner, yielding mixture of free phenols, separable by flash column chromatography (silica gel, hexanes/ethyl acetate, gradient elution), to give 14.0 mg (46%) of the less polar 1R,3R diastereomer (56), along with 13.0 mg (43%) of the more polar 1S,3R diastereomer (57) as white solids. Data for 56: $^1$H NMR (400MHz, CDCl$_3$) δ0.93 and 1.12 (2s, 2×3H, geminal-CH$_3$'s), 1.70 (m, 2H, 1-H), 1.94 (m, 3H, 6,3-H), 2.65 and 3.00 (d of ABq, 2H, $J_{AB}$=14.0 Hz, $J_A$=3.1 Hz, $J_B$=14.0 Hz, benzylic-CH$_2$) 3.84 (s, 3H, OCH$_3$), 4.37 (br s, 1H, 5-H), 4.39 and 4.92 (2s, 2×1H, methylidene-CH$_2$), 6.58 (s, 1H, 6'-H), 7.02 ppm (s, 1H, 3'-H). Data for 57: $^1$H NMR (400 MHz, CDCl$_3$) δ1.00 and 1.02 (2s, 2×3H, geminal-CH$_3$'s), 2.45 (dd, 1H, J=11.5, 3.2 Hz, 3-H), 2.70 and 2.88 (d of ABq, 2H, $J_{AB}$=14.1 Hz, $J_A$=13.1 Hz, $J_B$=4.2 Hz, benzylic-CH$_2$) 3.80 (s, 3H, OCH$_3$), 4.40 (br dd, 1H, J$_{13}$11.5, 4.5 Hz, 5-H), 4.47 and 4.86 (2s, 2×1H, methylidene-CH$_2$). 6.61 (s, 1H, 6'-H), 7.94 ppm (s, 1H, 3'-H). [Compound 56 is hereinafter also referred to as COMPOUND "R" or 120243]

EXAMPLE 25

(1S,3S)-1-Hydroxy-2-methylidene-3-(2'-hydroxy-4'-bromo-5'-methoxyphenyl)methyl-4,4-dimethylcyclohexane (59) and (1R,3S)-1-Hydroxy-2-methylidene-3-(2'-hydroxy-4'-bromo-5'-methoxyphenyl)methyl-4,4-dimethylcyclohexane (60):

This set of diastereomeric alcohols was prepared from (2S)-1-methylidene-2-[2'-(tert-butyl)dimethylsilyloxy-4'-bromo-5'-methoxyphenyl]methyl-3,3-dimethylcyclohexane (51) (0.340 g, 0.75 mmol) in the manner previously described for the synthesis of alcohol 54, affording 302 mg (86%) of an inseparable 1:1 mixture of diastereomeric allylic alcohols (58). A portion (21.6 mg, 0.046 mmol) of this diastereomeric mixture was subjected to deprotection of the silylphenol in the usual manner, yielding mixture of free phenols, separable by flash column chromatography (silica gel, hexanes/ethyl acetate, gradient elution), to give 7.2 mg (44%) of the less polar 1S,3S diastereomer (59), along with 6.5 mg (40%) of the more polar 1R,3S diastereomer (60) as white solids. The 400MHz $^1$H NMR spectrum and TLC. elution properties of each diastereomer 59 and 60 were identical to those previously reported for their respective enantiomeric hydroxy compounds 56 and 57. [Compound 59 is hereinafter also referred to as COMPOUND "B" or 120263]

EXAMPLE 26

(3S)-2-Methylidene-3-(2'-hydroxy-4'-bromo-5'-methoxyphenyl)methyl-4,4-dimethylcyclohexan-1-one (61):

To a flame-dried 50 mL round-bottomed flask containing a 1:1 mixture of silyl-protected phenols 58 (165.0 mg, 0.352 mmol) in 12 mL dichloromethane with 2% pyridine at room temperature was added Dess-Martin periodinane reagent (165 mg, 0.386 mmol, 1.1 equiv), and the mixture was stirred for 30 min. The reaction mixture was then transferred to a 125 mL erlynmeyer flask containing 50 mL 1:1 saturated aqueous NaHCO$_3$/10% Na$_2$S$_2$O$_3$, and the mixture was stirred for an additional 90 min. The mixture was then extracted with dichloromethane (2×40 mL), and the organic phase was washed with brine, dried over Na$_2$SO$_4$, and concentrated under diminished pressure. Purification by flash column chromatography (silica gel, hexanes/ethyl acetate, 9:1) afforded 150 mg (91%) of the desired enone as a white solid. $^1$H NMR (400MHz, CDCl$_3$) δ0.23 (s, 6H, Si(CH$_3$)$_2$], 1.00 [s, 9H, SiC(CH$_3$)$_3$], 1.12 and 1.15 (2s, 2×3H, geminal-CH$_3$'s), 1.62 (dddd, 1H, J=9.9, 6.6, 5.4, 1.3 Hz, 1-H$_{eq}$), 2.01 (dddd, 1H, J=14.0, 13.8, 8.9, 2.3 Hz, 1-H$_{ax}$), 2.24 and 2.50 (d of ABq, 2H, $J_{AB}$=11.9 Hz, $J_A$=11.9 Hz, $J_B$=2.8 Hz, benzylic-CH$_2$), 2.46 and 2.48 (ABq, 2H, $J_{AB}$=5.4 Hz, 6-H), 3.07 (dd, 1H, J=13.3, 3.6 Hz, 3-H), 3.80 (s, 3H, OCH$_3$), 4.46 (d, 1H, J=1.6 Hz) and 5.54 (d, 1H, J=1.8 Hz) [methylidene-CH$_2$], 6.41 (s, 1H, 6'-H), 6.93 ppm (s, 1H, 3'-H).

(1R,3S)-1-Hydroxy-2-methylidene-3-(2'-hydroxy-4'-bromo-5'-methoxyphenyl)methyl-1,4,4-trimethylcyclohexane (62) and (1S,3S)-1-Hydroxy-2-methylidene-3-(2'-hydroxy-4'-bromo-5'-methoxyphenyl)methyl-1,4,4-trimethylcyclohexane (63):

To a flame-dried 50 mL round-bottomed flask containing a solution of (3S)-2-methylidene-3-(2-hydroxy-4'-bromo-5'-methoxyphenyl)methyl-4,4-dimethylcyclohexan-1-one (61) (150.0 mg, 0.322 mmol) in 15 mL THF at −70° C. under nitrogen atmosphere was added methyllithium (0.60 mL of a 1.40M solution in ether, 0.840 mmol, 2.61 equiv), and the mixture was allowed to stir for 5 min before quenching with saturated aqueous NH$_4$C$_1$. Upon warming to room temperature, the reaction mixture was extracted with ethyl acetate, and the organic phase was washed with brine, dried over Na$_2$SO$_4$, and concentrated under diminished pressure gave a 3:1 (1R,3S: 1S,3S) mixture of the diastereomeric tertiary hydroxyls. Purification by flash column chromatography (silica gel, hexanes/ethyl acetate, gradient elution) afforded 28 mg (18%) of the less polar, minor 1S,3S isomer (63), along with 88 mg (57%) of the more polar, major 1R,3S isomer (62), as well as 30.2 mg (20%) recovered starting material. The diastereomeric alcohols were then independently converted to the corresponding free phenols in the usual manner, providing the trans, 1R,3S isomer (62) 1H NMR (400MHz, CDCl$_3$) δ0.84 and 1.04 (2s, 2×3 H, geminal-CH$_3$'s), 1.39 (s, 3H, 5-CH$_3$), 2.43 (br dd, 1H, J__11.3, 2.9 Hz, 3-H), 2.72 and 2.85 (d of ABq, 2H, $J_{AB}$=16.1 Hz, $J_A$=3.1 Hz, $J_B$=11.5 Hz, benzylic-CH$_2$) 3.77 (s, 3H, OCH$_3$), 4.57 and 5.16 (2s, 2×1H, methylidene-CH$_2$), 6.63 (s, 1H, 6'-H), 6.93 ppm (s, 1H, 3'-H); and the cis, 1S,3S isomer (63) $^1$H NMR (400MHz, CDCl$_3$) δ0.77 and 1.08 (2s, 2×3H, geminal-CH$_3$'s), 1.36 (s, 3H, 5-CH$_3$), 2.65 and 2.82 (d of ABq, 2H, $J_{AB}$=16.0 Hz, $J_A$=3.0 Hz, $J_B$=11.8 Hz, benzylic-CH$_2$), 2.97 (br dd, 1H, J=11.7, 2.5 Hz, 3-H), 3.79 (s, 3H, OCH$_3$), 4.64 and 4.96 (2s, 2×1H, methylidene-CH$_2$), 6.73 (s, 1H, 6'-H), 6.92 ppm (s, 1H, 3'-H). [Compound 63 is hereinafter also referred to as COMPOUND "J" or 120286, and Compound 62 is hereinafter also referred to as COMPOUND "P" or 120273]

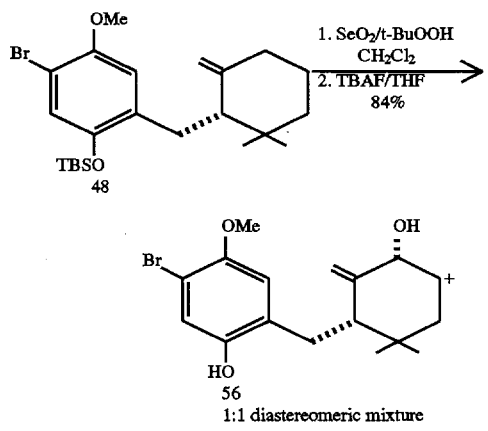

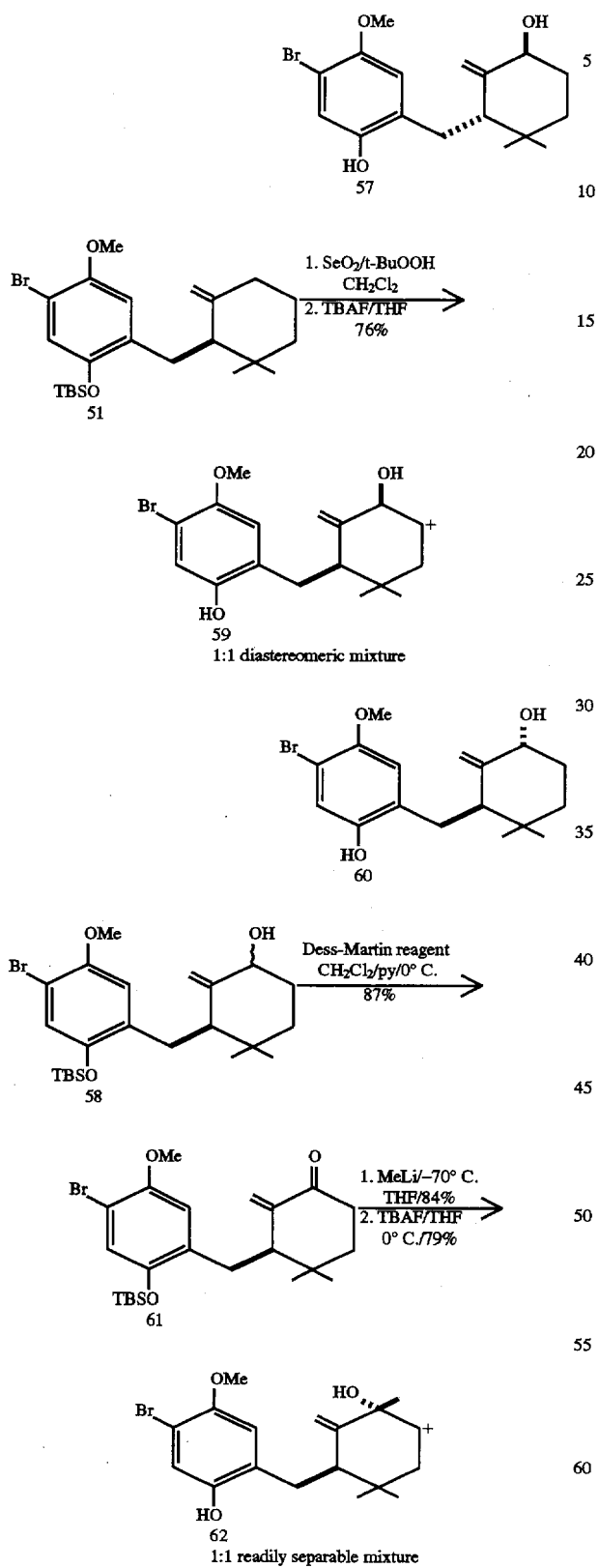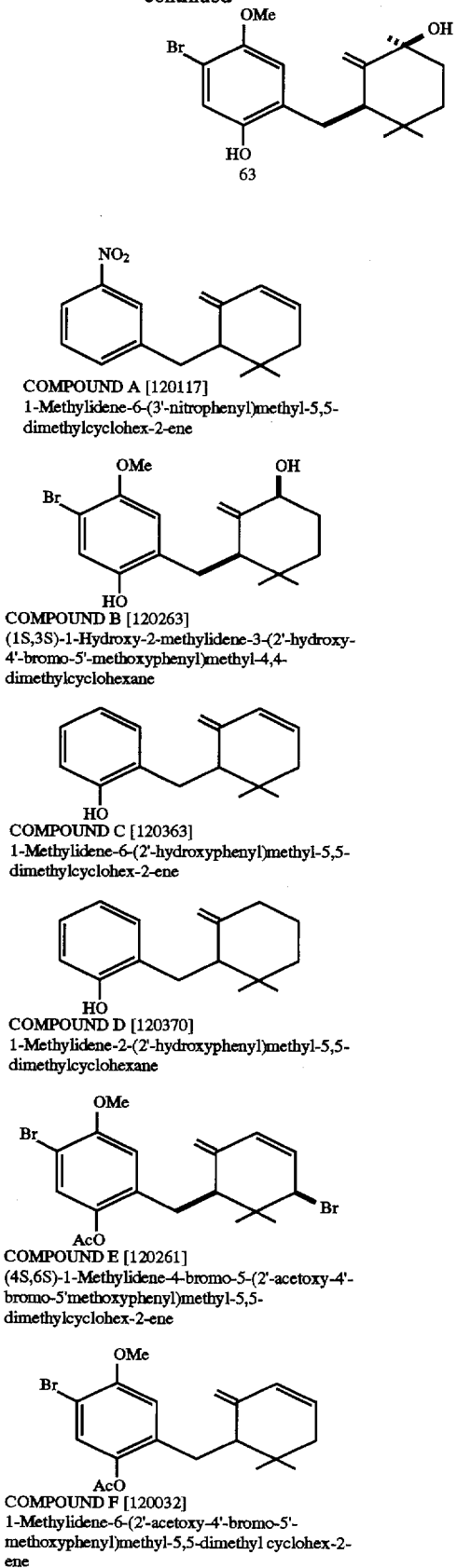

-continued

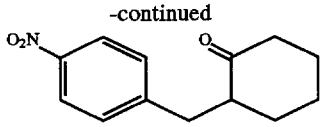

COMPOUND G [120138]
2-(4'-Nitrophenyl)methylcyclohexan-1-one

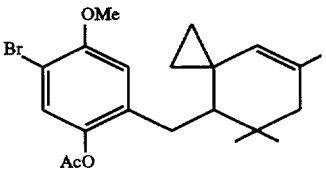

COMPOUND H [120299]
8-(2'-Acetoxy-4'-bromo-5'-methoxyphenyl)methyl-5,7,7-trimethylspiro[2.5]oct-4-ene

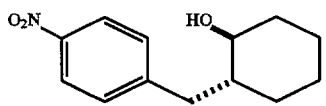

COMPOUND I [120154]
trans-2-(4'-Nitrophenyl)methylcyclohexan-1-ol

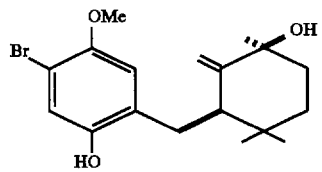

COMPOUND J [120286]
(1S,3S)-1-Hydorxy-2-methylidene-3-(2'-hydroxy-4'-bromo-5'-methoxyphenyl)methyl-1,4,4-trimethylcyclohexane

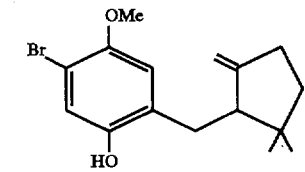

COMPOUND K [120192]
1-Methylidene-2-(2'-hydroxy-4'-bromo-5'-methoxyphenyl)methyl-3,3-dimethyylcyclopentane

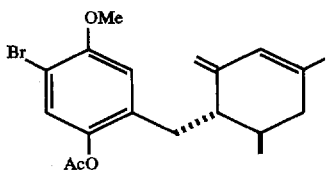

COMPOUND L (120260)
(5R,6S)-1-Methylidene-6-(2'-acetoxy-4'-bromo-5'-methoxyphenyl)methyl-5-methylcyclohex-2-ene

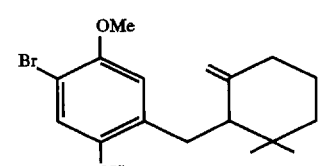

COMPOUND M [120019]
1-Methylidene-2-(2'-hydroxy-4'-bromo-5'-methoxyphenyl)methyl-3,3-dimethylcyclohexane -continued

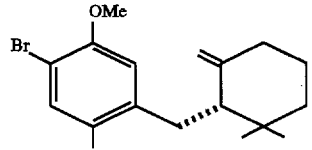

COMPOUND N [120037]
(2R)-1-Methylidene-2-(2'-hydroxy-4'-bromo-5'-methoxyphenyl)methyl-3,3-dimethylcyclohexane

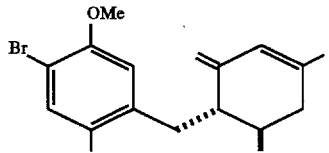

COMPOUND O [120276]
(5R,6S)-1-Methylidene-6-(2'-acetoxy-4'-bromo-5'-methoxyphenyl)methyl-3,5-dimethylcyclohex-2-ene

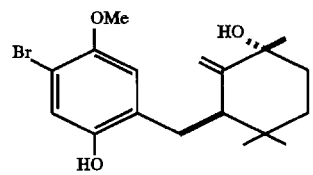

COMPOUND P [120273]
(1R,3S)-1-Hydroxy-2-methylidene-3-(2'-hydroxy-4'-bromo-5'-methoxyphenyl)methyl-1,4,4-trimethylcyclohexane

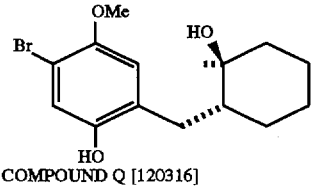

COMPOUND Q [120316]
trans-1-Methyl-2-(2'-hydroxy-4'-bromo-5'-methoxyphenyl)methylcyclohexan-1-ol

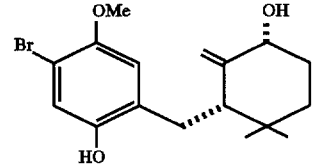

COMPOUND R [120243]
(1R,3R)-1-Hydroxy-2-methylidene-3-(2'-hydroxy-4'-bromo-5'-methoxyphenyl)methyl-4,4-dimethylcyclohexane

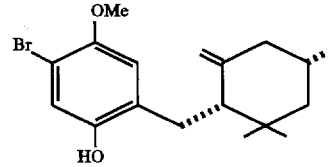

COMPOUND S [120275]
cis-1-Methylidene-2-(2'-hydroxy-4'-bromo-5'-methoxyphenyl)methyl-3,3,5-trimethyl cyclohexane

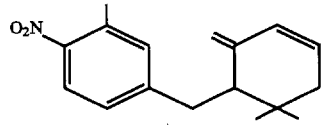

-continued

COMPOUND T [120120]
1-Methylidene-6-(3'-methyl-4'-nitrophenyl)
methyl-5,5-dimethylcyclohex-2-ene

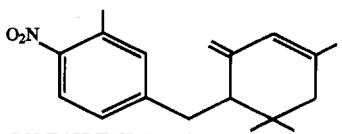

COMPOUND U [120168]
1-Methylidene-6-(3'-methyl-4'-nitrophenyl)
methyl-3,5,5-trimethylcyclohex-2-ene

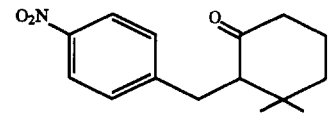

COMPOUND V [120211]
2-(4'-Nitrophenyl)methyl-3,3-dimethylcyclohexan-1-one

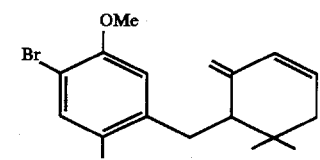

COMPOUND W [120033]
1-Methylidene-6-(2'-hydroxy-4'-bromo-5'-methoxyphenyl)methyl-5,5-dimethylcyclohex-2-ene

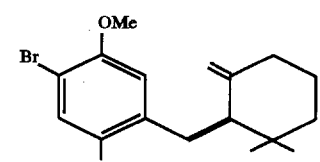

COMPOUND X [120058]
(2S)-1-Methylidene-2-(2'-hydroxy-4'-bromo-5'-methoxyphenyl)methyl-3,3-dimethylcyclohexane

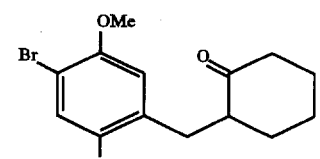

COMPOUND Y [120125]
2-(2'-Hydroxy-4'-bromo-5'-methoxyphenyl)
methylcyclohex-1-one

Androgen Receptor Activity

Utilizing the "cis-trans" or "co-transfection" assay described by Evans et al., Science, 240:889–95 (May 13, 1988), the disclosure of which is herein incorporated by reference, the derivative compounds of Examples 1–26 were tested and found to have strong, specific antagonist activity for the intracellular receptor for androgen. This assay is described in further detail in U.S. Pat. Nos. 4,981,784 and 5,071,773, the disclosures of which are incorporated herein by reference. The co-transfection assay provides a method for identifying functional ligands (either agonists which mimic, or antagonists which inhibit, the effect of hormones), and quantifying their activity for ligand-responsive receptor proteins. In this regard, the co-transfection assay mimics an in vivo system in the laboratory. Importantly, activity in the co-transfection assay correlates very well with known in vivo activity, such that the co-transfection assay functions as a quantitative predicator of a tested compounds in vivo pharmacology. See, e.g., T. Berger et al. 41 *J. Steroid Biochem. Molec. Biol.* 773 (1992), the disclosure of which is herein incorporated by reference.

In the co-transfection assay, a cloned gene for an intracellular receptor (e.g., androgen receptor) is introduced by transfection (a procedure to induce cells to take up foreign genes) into a background cell substantially devoid of endogenous intracellular receptors. This introduced gene directs the recipient cells to make the intracellular receptor protein. A second gene is also introduced (co-transfected) into the same cells in conjunction with the intracellular receptor gene. This second gene functions as a reporter for the transcription-modulating activity of the target intracellular receptor. Thus, the reporter acts as a surrogate for the products normally expressed by a gene under control of the target receptor and its natural hormone. A preferred reporter gene is one which expresses the firefly enzyme luciferase.

The co-transfection assay can detect small molecule agonists or antagonists of target intracellular receptors. Exposing the cells to an agonist ligand increases reporter activity in the transfected cells. This activity can be conveniently measured, e.g., by increasing luciferase production, which reflects ligand-dependent, intracellular receptor-mediated increases in reporter transcription. To detect antagonists, the co-transfection assay is carried out in the presence of a constant concentration of an agonist (e.g., for androgen receptor, dihydrotestosterone) known to induce a defined reporter signal. Increasing concentrations of a test antagonist will decrease the reporter signal (e.g., luciferase production). The co-transfection assay is therefore useful to detect both agonists and antagonists of specific intracellular receptors. It determines not only whether a compound interacts with a particular intracellular receptor, but whether this interaction mimics (agonizes) or blocks (antagonizes) the effects of the natural regulatory molecules on target gene expression, as well as the specificity and strength of this interaction.

Co-transfected cells are exposed to a medium to which is added the potential ligand (compound) that is being evaluated. If the candidate compound diffuses into the cell, binds to the receptor, and the resulting receptor complex functions as an agonist, it will subsequently bind to the co-transfected reporter gene and initiate transcription. Typically, the reporter gene is one that expresses luciferase, which is capable of catalyzing a light-emitting reaction with its substrate luciferin. Thus, after cell lysis and the introduction of luciferin, the amount of light produced relative to the concentration of candidate compound used in the assay provides a measure of the potency and efficacy of the compound tested. Antagonist activity is evaluated by adding the candidate ligand and a known agonist to the co-transfected cells. Suppression of agonist-induced luciferase production by the candidate compound, and hence the amount of light produced, indicates the candidate compound is an antagonist.

The androgen receptor activity of the derivative compounds of Examples 1–26 were demonstrated according to the following illustrative Examples.

EXAMPLE 27

Plasmid pRShAR (produced by cloning the 3400 bp linear fragment of the human androgen receptor (hAR) from vector pGEM3Z (85 *P.N.A.S.* 7211 (1988)) into the Bam HI site of the pRS vector), which expresses the human androgen receptor was transfected into monkey kidney fibroblast (CV-1) cells along with reporter plasmid MTV-LUC. via calcium phosphate precipitation as described in Berger et at. supra. After six hours, the cells were washed with phosphate-buffered saline (PBS) and incubated at 37° C. with 95% $O_2$/5% $CO_2$ for 40 hours prior to harvest.

After incubation, whole cell receptor extract was prepared by homogenizing the harvested cells in Tris-HCl buffer, pH=7.4, containing 30% glycerol, 1 mM EDTA, 12 mM monothioglycerol, 1 mM PMSF, and 0.5M potassium chloride. The homogenate was incubated at 4° C. for 60 min with resuspension every 10 min. The suspension was centrifuged (105,000× g, 60 min) and the supernatant was collected and flash frozen in liquid nitrogen and stored frozen at −70° C.

Aliquots of the whole cell extract containing transfected androgen receptor were incubated at 4° C. for 24 hours with a constant concentration (5 nM) of tritiated dihydrotestosterone (DHT) and increasing concentrations (0–2.5×10$^{-5}$M) of the derivative Compounds A–Y. The concentration of bound tritiated progesterone was determined in each sample by the dextran-coated charcoal adsorption technique, as follows.

To a 500 µl final volume incubation mixture, 400 gl of 7.5% (w/v) dextran-coated charcoal suspension in gelatin phosphate buffer was added. The mixture was vortexed and incubated at 4° C. for 10 min and then centrifuged at 3000 rpm for 10 min. The amount of bound tritiated hormone was determined by liquid scintillation spectrophotometry of an aliquot of the supernatant.

Figure 2:
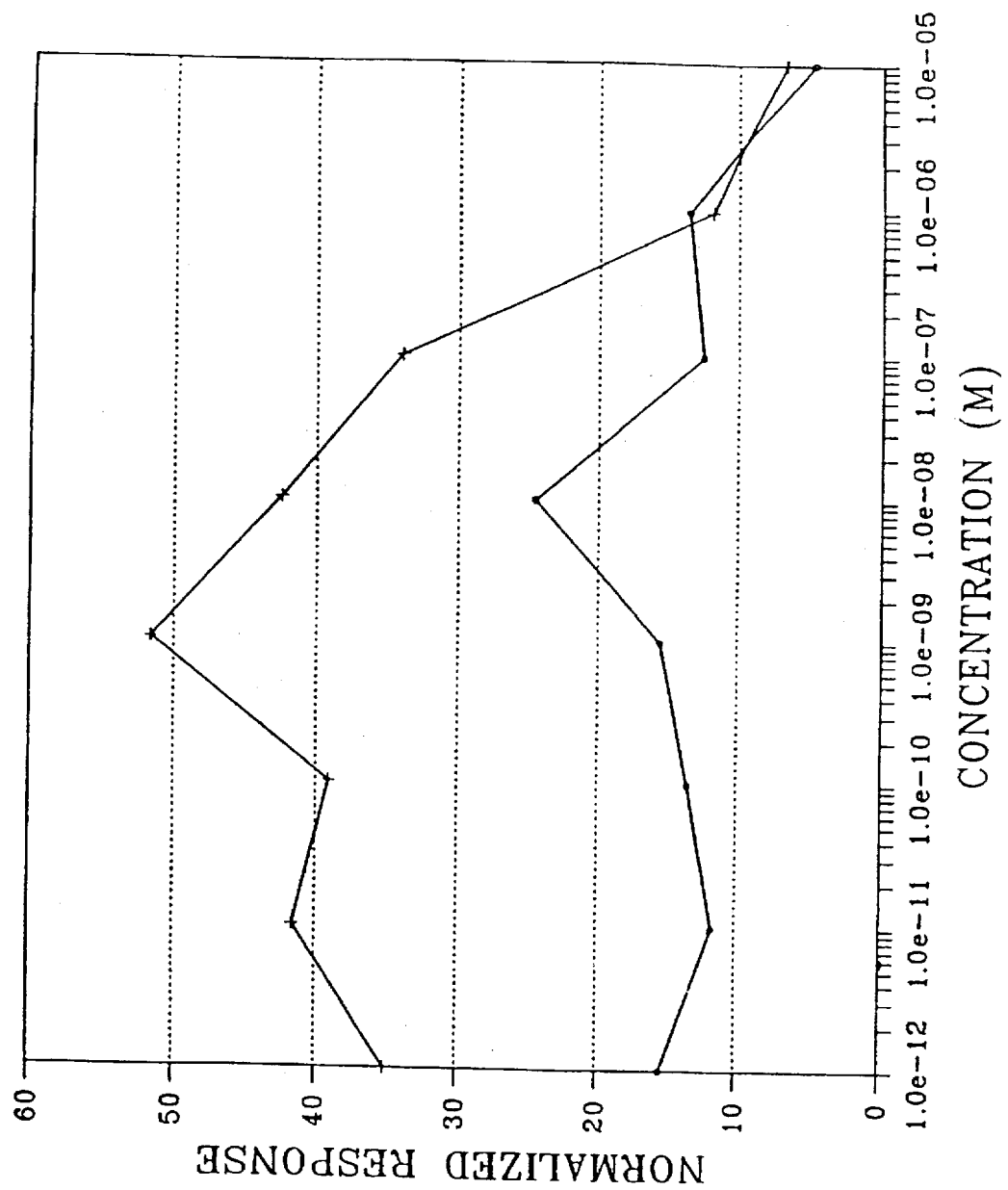
FIG. 2 presents antagonist activation profiles for analysis of androgen receptor by derivative compound "A" (•) and for derivative compound "B" (+)
Figure 3:
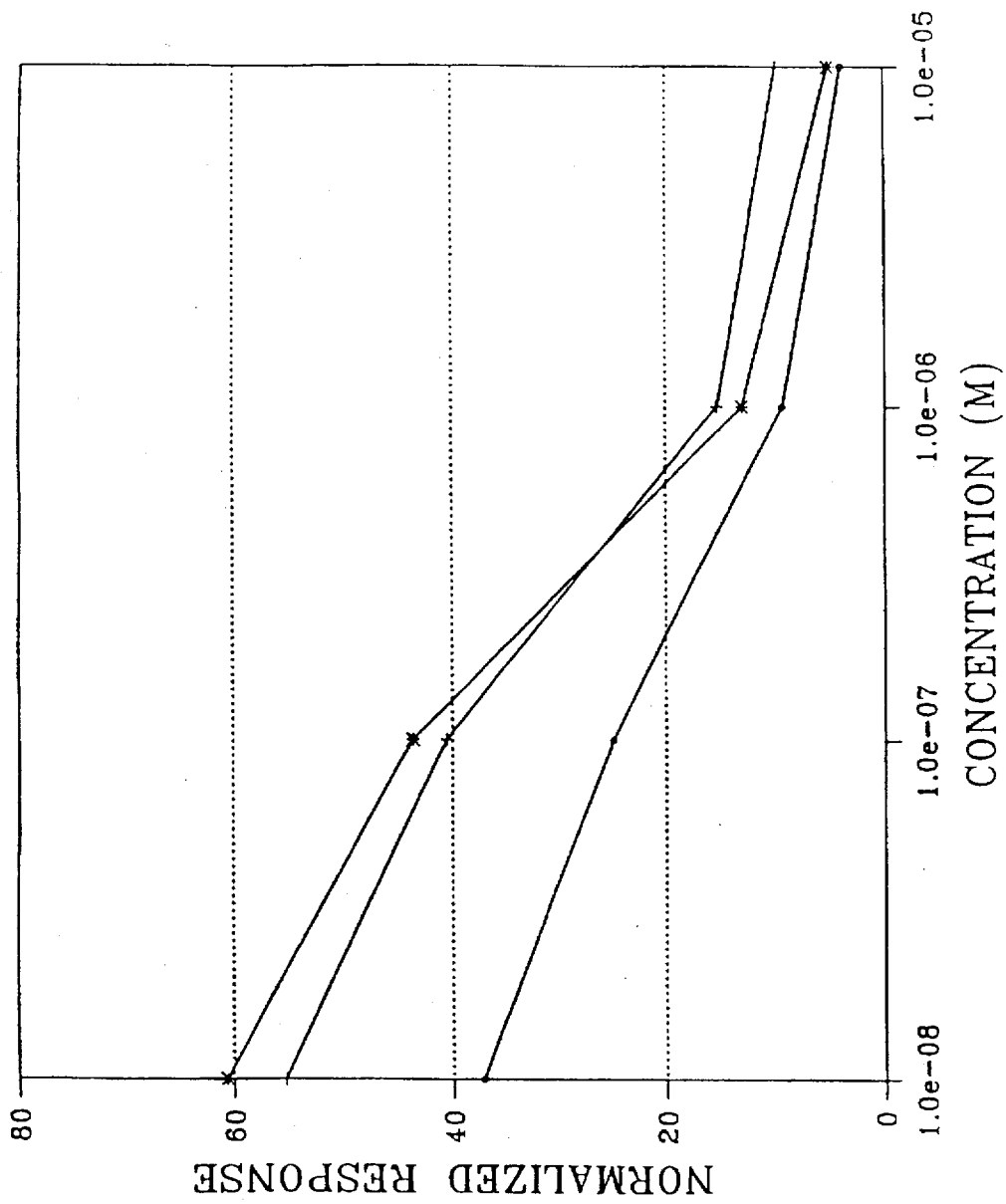
FIG. 3 presents antagonist activation profiles for analysis of androgen receptor by derivative compound "B" (•), derivative compound "C" (+), and derivative compound "D"(*).

The androgen antagonist activity assay results are shown below in Table 1. Efficacy is reported as the % maximal response observed for each compound relative to 2-Hydroxy-flutamide, a compound known to exhibit androgen receptor antagonist activity. Also reported in Table 1 for each compound is its potency or $IC_{50}$ (which is the concentration (nM), required to reduce the maximal response by 50%). Furthermore, the full androgen antagonist dose response profile of Compounds "A, B, C. & D" are shown in FIGS. 2 and 3, relative to the antagonist dose response profile of 2-Hydroxy-flutamide, as shown in FIG. 1. In this regard, the androgen antagonist compounds of the present invention preferably show greater than 60% efficacy and are potent at less than 800 nM, more preferably show greater than 70% efficacy and are potent at less than 500 nM, and most preferably show efficacy of greater than 80% and are potent at less than 300 nM as antagonists to the androgen receptor. Further, the compounds of the present invention selectivity as androgen antagonist is preferably shown by a potency at least three times greater, and more preferably at least five times greater than that found on other intracellular receptors (e.g., progesterone receptor, glucocorticoid receptor etc.).

The specific activity of Compounds A–J was compared relative to their antagonist activity on the human progesterone receptor (PR) utilizing CV-1 cells cotransfected with plasmid pRShPR-B, as altered at the Tau-1 location (e.g., PR-TI)[specifically, hPR-B was excised from the vector pGEM3Z (69 Cell 703 (1992)); the Tau-1 fragment of the gluccocorticoid receptor was inserted into hPR-B at the unique HincII site in the N-terminal region; a Bst EII to BST bI fragment spanning the Tau-1 insertion was then used to replace the corresponding region in pRShPR-B]. A comparison of the AR and PR activity of Compounds A–J is shown in Table 2. Efficacy on PR-TI is reported as the % maximal response observed for each compound, and is comparable to that found with RU-486, a compound known to exhibit progesterone receptor antagonist activity. Potency or $IC_{50}$ is as reported for AR-wt transfected CV-1 cells. As can be seen, the high specific activity androgen antagonist compounds of the present invention are, in almost all circumstances, at least several times less potent (e.g., require a much higher potency to achieve the same activity), and are often less efficacious as a progesterone antagonist.

TABLE 1

Inhibitory $IC_{50}$ Efficacy (%) and Potency (nM) of Example Compounds A-Y as Androgen Antagonists.

| Compound | Efficacy (%) | Potency (nM) |
| --- | --- | --- |
| A | 69 | 66 |
| B | 85 | 180 |
| C | 82 | 210 |
| D | 92 | 220 |
| E | 60 | 230 |
| F | 87 | 240 |
| G | 79 | 250 |
| H | 89 | 250 |
| I | 85 | 290 |
| J | 85 | 300 |
| K | 91 | 330 |
| L | 88 | 370 |
| M | — | — |
| N | 90 | 378 |
| O | 78 | 390 |
| P | 88 | 420 |
| Q | 94 | 460 |
| R | 70 | 500 |
| S | 92 | 500 |
| T | 88 | 545 |
| U | 69 | 565 |
| V | 85 | 590 |
| W | 89 | 610 |
| X | 88 | 723 |
| Y | 67 | 340 |

TABLE 2

| | CV-1 Cells AR-wt | | CV-1 Cells PR-TI | |
| --- | --- | --- | --- | --- |
| Compound | Efficacy (%) | Potency (nM) | Efficacy (%) | Potency (nM) |
| A | 69 | 66 | 45 | 3800 |
| B | 85 | 180 | 98 | 865 |
| C | 82 | 210 | 20 | >10,000 |
| D | 92 | 220 | 73 | 3,500 |
| E | 60 | 230 | 20 | >10,000 |
| F | 87 | 240 | 53 | 820 |
| G | 79 | 250 | 98 | 920 |
| H | 89 | 250 | 26 | 160 |
| I | 85 | 290 | 99 | 360 |
| J | 85 | 300 | 95 | 850 |

The derivative compounds were also individually tested for cross-reactivity with the other known intracellular receptor classes. This testing showed the compounds not to have significant activity with the glucocorticoid receptor, mineralocorticoid receptor or estrogen receptor.

Pharmacological and Other Applications

As previously discussed, it has been recognized that the co-transfection assay provides a functional assessment of the ligand (compound) being tested as either an agonist or antagonist of the specific genetic process sought to be affected, and mimics an in vivo system in the laboratory. Compounds which do not react with other intracellular receptors, as determined by the co-transfection assay, can be expected to result in fewer pharmacological side effects. Because the co-transfection assay is conducted in living cells, the evaluation of a compound provides an early indicator of the potential toxicity of the candidate compound at concentrations where a therapeutic benefit would be expected.

As will be discernible to those skilled in the art, the non-steroid androgen receptor antagonist compounds disclosed can be readily utilized in pharmacological applications where androgen receptor antagonist activity is desired, and where it is desired to minimize cross reactivities with other related intracellular receptors. In vivo applications of the invention include administration of the disclosed compounds to mammalian subjects, and in particular to humans.

The compounds of the present invention are small molecules which are relatively fat soluble or lipophilic and enter the cell by passive diffusion across the plasma membrane. Consequently, these compounds are well suited for administration orally as well as by injection. Upon administration, these compounds can selectively antagonize androgen receptors and thereby modulate processes mediated by these receptors.

The pharmaceutical compositions of this invention are prepared in conventional dosage unit forms by incorporating an active compound of the invention, or a mixture of such compounds, with a nontoxic pharmaceutical carrier according to accepted procedures in a nontoxic amount sufficient to produce the desired pharmacodynamic activity in a mammalian and in particular a human subject. Preferably, the composition contains the active ingredient in an active, but nontoxic, amount selected from about 5 mg to about 500 mg of active ingredient per dosage unit. This quantity depends on the specific biological activity desired and the condition of the patient.

The pharmaceutical carder or vehicle employed may be, for example, a solid or liquid. A variety of pharmaceutical forms can be employed. Thus, when using a solid carder, the preparation can be plain milled micronized in oil, tableted, placed in a hard gelatin or enteric-coated capsule in micronized powder or pellet form, or in the form of a troche, lozenge, or suppository. When using a liquid carder, the preparation can be in the form of a liquid, such as an ampule, or as an aqueous or nonaqueous liquid suspension. The following examples provide illustrative pharmacological composition formulations:

EXAMPLE 28

Hard gelatin capsules are prepared using the following ingredients:

| | Quantity (mg/capsule) |
|---|---|
| 1-methylidene-6-(3'-nitrophenyl)methyl-5,5-dimethylcyclohex-2-ene (Compound A) | 140 |
| Starch, dried | 100 |
| Magnesium stearate | 10 |
| Total | 250 mg |

The above ingredients are mixed and filled into hard gelatin capsules in 250 mg quantifies.

EXAMPLE 29

A tablet is prepared using the ingredients below:

| | Quantity (mg/tablet) |
|---|---|
| Compound A | 140 |
| Cellulose, microcrystalline | 200 |
| Silicon dioxide, fumed | 10 |
| Stearic acid | 10 |
| Total | 360 mg |

The components are blended and compressed to form tablets each weighing 665 mg.

EXAMPLE 30

Tablets, each containing 60 mg of active ingredient, are made as follows:

| | Quantity (mg/tablet) |
|---|---|
| Compound A | 60 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 150 mg |

The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate, and talc, previously passed through a No. 60 mesh U.S. sieve, and then added to the granules which, after mixing, are compressed on a tablet machine to yield tablets each weighing 150 mg.

EXAMPLE 31

Suppositories, each containing 225 mg of active ingredient, may be made as follows:

| | |
|---|---|
| Compound A | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2g capacity and allowed to cool.

EXAMPLE 32

An intravenous formulation may be prepared as follows:

| | |
|---|---|
| Compound A | 100 mg |
| Isotonic saline | 1,000 mL |
| Glycerol | 100 mL |

The compound is dissolved in the glycerol and then the solution is slowly diluted with isotonic saline. The solution of the above ingredients is then administered intravenously at a rate of 1 mL per minute to a patient.

The compounds of this invention also have utility when labeled as ligands for use in assays to determine the presence of androgen receptor. They are particularly useful due to their ability to selectively activate androgen receptor, and can therefore be used to determine the presence of such receptors in the presence of other related receptors.

Due to the selective specificity of the compounds of this invention for androgen receptor, these compounds can be used to purify samples of androgen receptor in vitro. Such purification can be carried out by mixing samples containing androgen receptor with one or more of the derivative compounds disclosed so that the compound (ligand) binds to the receptor, and then separating out the bound ligand/receptor combination by separation techniques which are known to those of skill in the art. These techniques include column separation, filtration, centrifugation, tagging and physical separation, and antibody complexing, among others.

While in accordance with the patent statutes, description of the preferred weight fractions, and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

We claim:

1. A method of antagonizing androgen activity comprising the in vivo administration of one or more of the compounds exhibiting activity as an androgen receptor antagonist having the formulae:

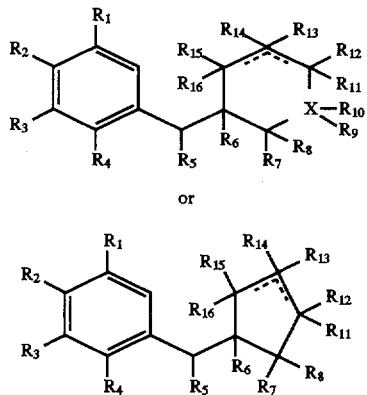

wherein:
the dotted lines in the structure depict optional double bonds;
X is carbon;
$R_1$ is $R_{17}$, —$OR_{17}$, —$N(R_{17'})$, —$SR_{17}$, fluorine, chlorine, bromine, or —$NO_2$;
$R_{17}$ and $(R_{17'})$, each independently, are hydrogen, saturated or unsaturated $C_1$–$C_6$ alkyl, $C_3$–$C_7$ cycloalkyl, $C_5$–$C_7$ aryl, or $C_7$ aralkyl, said alkyl groups being branched or straight-chain;
$R_2$ is —$NO_2$, —$N(OH)R_{17}$, fluorine, chlorine, bromine, iodine, $R_{17}$, —$N(R_{17})$ $(R_{17'})$, —$SR_{17}$, —$S(O)_2$—$R_{17}$, —$CH_2OH$, —$C(O)$—$H$, —$C(O)CH_3$, —$C(O)$—$OCH_3$, —$CH=CH_2$, —$CH=CH$—$C(O)$ —$C(O)_3$, or $R_{18}$;
$R_{18}$ and $(R_{18'})$, each independently, are hydrogen, saturated or unsaturated $C_1$–$C_6$ alkyl, $C_3$–$C_7$ cycloalkyl, $C_5$–$C_7$ aryl, or $C_7$ aralkyl, said alkyl groups being branched or straight-chain which optionally may contain hydroxyl, aldehyde, ketone, nitrile, or ester groups;
$R_3$ is $R_{17}$ or —$OR_{17}$;
$R_4$ is hydrogen, —$OR_{17}$, —$OC(O)R_{17}$, —$OC(O)OR_{17}$, —$OC(O)N(R_{17})$ $(R_{17'})$, —$OS(O)_2R_{17}$, or —$OS(O)$—$R_{17}$, except that $R_1$, $R_2$, $R_3$, and $R_4$ cannot all be hydrogen, and $R_1$ cannot be $OCH_3$ when $R_2$, $R_3$, and $R_4$ are each hydrogen;
$R_5$ is hydrogen;
$R_6$ is $R_{17}$;
$R_7$ $R_8$, each independently, are $R_{18}$, or $R_7$ and $R_8$ together are a carbocyclic 3–8 member ring, but $R_7$ and $R_8$ cannot both be hydrogen in the second of the two above structures;
$R_9$ and $R_{10}$, each independently, are chlorine, bromine, or $R_{17}$, or $R_9$ and $R_{10}$ combined are =O, except when X=O, $R_9$ and $R_{10}$ are not present, and except that neither $R_9$ or $R_{10}$ can be bromine when $R_1$ is methoxy, $R_2$ is bromo, $R_3$ is hydrogen, $R_4$ is hydroxy, $R_5$ and $R_6$ are hydrogen, and $R_7$ and $R_8$ are methyl, $R_{11}$–$R_{14}$ are hydrogen, and $R_{15}$ and $R_{16}$ together are methylene;
$R_{11}$ and $R_{12}$, each independently, are —$OR_{17}$, $R_{18}$, are =O, or are =$CH_2$, except when $R_{11}$ is attached to an $sp^2$ carbon atom in the ring, then $R_{12}$ is not present and $R_{11}$ is $R_{18}$,
or $R_{11}$ and $R_{13}$ together are joined in a carbocyclic 3–8 member ring or are —O— to form an epoxide;
$R_{13}$ and $R_{14}$, each independently, are —$OR_{17}$ or $R_{18}$, except when $R_{13}$ is attached to an $sp^2$ carbon atom in the ring, then $R_{14}$ is not present and $R_{17}$ is —$OR_{17}$ or $R_{18}$;
$R_{15}$ and $R_{16}$, each independently, are $R_{18}$ except that $R_{15}$ and $R_6$ cannot both be H, or $R_{15}$ and $R_{16}$ together are —$CH_2$—$O$— forming an epoxide, or $R_{15}$ and $R_{16}$ combined are =O or =$C(R_{18})(R_{18'})$, except when $R_{15}$ and $R_{16}$ combined are =O then $R_7$ and $R_8$ cannot both be hydrogen, and except when $R_{15}$ is attached to an $sp^2$ carbon atom in the ring, then $R_{16}$ is not present, or $R_{15}$ and $R_{16}$ together are joined in a carbocyclic 3–8 member ring.

2. A method for treating a mammalian subject requiring androgen receptor antagonist therapy comprising administering to such subject a pharmaceutically effective amount of a compound exhibiting activity as an androgen receptor antagonist having the formulae:

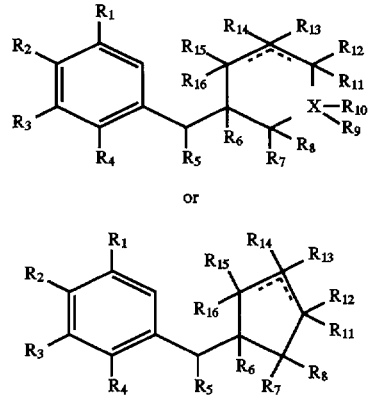

wherein:
the dotted lines in the structure depict optional double bonds;

X is carbon;

$R_1$ is $R_{17}$, —$OR_{17}$, —$N(R_{17})(R_{17'})$, —$SR_{17}$, fluorine, chlorine, bromine, or —$NO_2$, $R_{17}$ and ($R_{17'}$), each independently, are hydrogen, saturated or unsaturated $C_1$–$C_6$ alkyl, $C_3$–$C_7$ cycloalkyl, $C_5$–$C_7$ aryl, or $C_7$ aralkyl, said alkyl groups being branched or straight-chain;

$R_2$ is —$NO_2$, —$N(OH)$ $R_{17}$, fluorine, chlorine, bromine, iodine, $R_{17}$, —$N(R_{17})$ $(R_{17'})$, —$SR_{17}$, —$S(O)$—$R_{17}$, —$S(O)_2$—$R_{17}$, —$CH_2OH$, —$C(O)$—H, —$C(O)CH_3$, —$C(O)$—$OCH_3$, —$CH$=$CH_2$, —$CH$=$CH$—$C(O)$—$OCH_3$, or $R_{18}$;

$R_{18}$ and ($R_{18'}$), each independently, are hydrogen, saturated or unsaturated $C_1$–$C_6$ alkyl, $C_3$–$C_7$ cycloalkyl, $C_5$–$C_7$ aryl, or $C_7$ aralkyl, said alkyl groups being branched or straight-chain which optionally may contain hydroxyl, aldehyde, ketone, nitrile, or ester groups;

$R_3$ is $R_{17}$ or —$OR_{17}$;

$R_4$ is hydrogen, —$OR_{17}$, —$OC(O)R_{17}$, —$OC(O)OR_{17}$, —$OC(O)N(R_{17})$ $(R_{17'})$, —$OS(O)_2R_{17}$, or —$OS(O)$—$R_{17}$, except that $R_1$, $R_2$, $R_3$, and $R_4$ cannot all be hydrogen, and $R_1$ cannot be $OCH_3$ when $R_2$, $R_3$, and $R_4$ are each hydrogen;

$R_5$ is hydrogen;

$R_6$ is $R_{17}$;

$R_7$ and $R_8$, each independently, are $R_{18}$, or $R_7$ and $R_8$ together are a carbocyclic 3–8 member ring, but $R_7$ and $R_8$ cannot both be hydrogen in the second of the two above structures;

$R_9$ and $R_{10}$, each independently, are chlorine, bromine, or $R_{17}$ or $R_9$ and $R_{10}$ combined are =O, except when X=O, $R_9$ and $R_{10}$ are not present, and except that neither $R_9$ or $R_{10}$ can be bromine and $R_1$ is methoxy, $R_2$ is bromo, $R_3$ is hydrogen, $R_4$ is hydroxy, $R_5$ and $R_6$ are hydrogen, and $R_7$ and $R_8$ are methyl, $R_{11}$–$R_{14}$ are hydrogen, and $R_{15}$ and $R_{16}$ together are methylene;

$R_{11}$ and $R_{12}$, each independently, are —$OR_{17}$, $R_{18}$, are =O, or are =$CH_2$, except when $R_{11}$ is attached to an $sp^2$ carbon atom in the ring, then $R_{12}$ is not present and $R_{11}$ is $R_{18}$, or $R_{11}$ and $R_{13}$ together are joined in a carbocyclic 3–8 member ring or are —O— to form an expoxide;

$R_{13}$ and $R_{14}$, each independently, are —$OR_{17}$ or $R_{18}$, except when $R_{13}$ is attached to an $sp^2$ carbon atom in the ring, then $R_{14}$ is not present and $R_{13}$ is —$OR_{17}$ or $R_{18}$;

$R_{15}$ and $R_{16}$, each independently, are $R_{18}$ except that $R_{15}$ and $R_{16}$ cannot both be H, or $R_{15}$ and $R_{16}$ together are —$CH_2$—O— forming an epoxide, or $R_{15}$ and $R_{16}$ combined are =O or =$C(R_{18})(R_{18'})$, except when $R_{15}$ and $R_{16}$ combined are =O then $R_7$ and $R_8$ cannot both be hydrogen, and except when $R_{15}$ is attached to an $sp^2$ carbon atom in the ring, then $R_{16}$ is not present, or $R_{15}$ and $R_{16}$ together are joined in a carbocyclic 3–8 member ring.

3. A method for modulating a process mediated by androgen receptors comprising causing said process to be conducted in the presence of at least one compound exhibiting activity as an androgen receptor antagonist having the formulae:

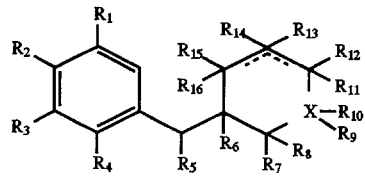

or

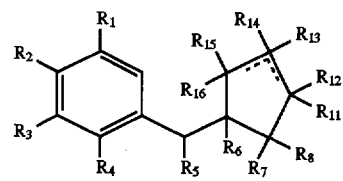

wherein:

the dotted lines in the structure depict optional double bonds;

X is carbon;

$R_1$ is $R_{17}$, —$OR_{17}$, —$N(R_{17})(R_{17'})$, —$SR_{17}$, fluorine, chlorine, bromine, or —$NO_2$;

$R_{17}$ and ($R_{17'}$), each independently, are hydrogen, saturated or unsaturated $C_1$–$C_6$ alkyl, $C_3$–$C_7$ cycloalkyl, $C_5$–$C_7$ aryl, or $C_7$ aralkyl, said alkyl groups being branched or straight-chain;

$R_2$ is —$NO_2$, —$N(OH)R_{17}$, fluorine, chlorine, bromine, iodine, $R_{17}$, —$N(R_{17})$ $(R_{17'})$, —$SR_{17}$, —$S(O)$—$R_{17}$, —$S(O)_2$—$R_{17}$, —$CH_2OH$, —$C(O)$—H, —$C(O)CH_3$, —$C(O)$—$OCH_3$, —$CH$=$CH_2$, —$CH$=$CH$—$C(O)$—$OCH_3$, or $R_{18}$;

$R_{18}$ and ($R_{18'}$), each independently, are hydrogen, saturated or unsaturated $C_1$–$C_6$ alkyl, $C_3$–$C_7$ cycloalkyl, $C_{5-7}$ aryl, or $C_7$ aralkyl, said alkyl groups being branched or straight-chain which optionally may contain hydroxyl, aldehyde, ketone, nitrile, or ester groups;

$R_3$ is $R_{17}$ or —$OR_{17}$;

$R_4$ is hydrogen, —$OR_{17}$, —$OC(O)R_{17}$, —$OC(O)OR_{17}$, —$OC(O)N(R_{17})$ $(R_{17'})$, —$OS(O)_2R_{17}$, or —$OS(O)$—$R_{17}$, except that $R_1$, $R_2$, $R_3$, and $R_4$ cannot all be hydrogen, and $R_1$ cannot be $OCH_3$ when $R_2$, $R_3$, and $R_4$ are each hydrogen;

$R_5$ is hydrogen;

$R_6$ is $R_{17}$;

$R_7$ and $R_8$, each independently, are $R_{18}$, or $R_7$ and $R_8$ together are a carbocyclic 3–8 member ring, but $R_7$ and $R_8$ cannot both be hydrogen in the second of the two above structures;

$R_9$ and $R_{10}$, each independently, are chlorine, bromine, or $R_{17}$, or $R_9$ and $R_{10}$ combined are =O, except when X=O, $R_9$ and $R_{10}$ are not present, and except that neither $R_9$ or $R_{10}$ can be bromine when $R_1$ is methoxy, $R_2$ is bromo, $R_3$ is hydrogen, $R_4$ is hydroxy, $R_5$ and $R_6$ are hydrogen, and $R_7$ and $R_8$ are methyl, $R_{11}$–$R_{14}$ are hydrogen, and $R_{15}$ and $R_{16}$ together are methylene;

$R_{11}$ and $R_{12}$, each independently, are —$OR_{17}$, $R_{18}$, are =O, or are =$CH_2$, except when $R_{11}$ is attached to an $sp^2$ carbon atom in the ring, then $R_{12}$ is not present and $R_{11}$ is $R_{18}$, or $R_{11}$ and $R_{13}$ together are joined in a carbocyclic 3–8 member ring or are —O— to form an expoxide;

$R_{13}$ and $R_{14}$, each independently, are —$OR_{17}$ or $R_{18}$, except when $R_{13}$ is attached to an $sp^2$ carbon atom in the ring, then $R_{14}$ is not present and $R_{13}$ is —$OR_{17}$ or $R_{18}$;

$R_{15}$ and $R_{16}$, each independently, are $R_{18}$ except that $R_{15}$ and $R_{16}$ cannot both be H, or $R_{15}$ and $R_{16}$ together are —$CH_2$—O— forming an epoxide, or $R_{15}$ and $R_{16}$ combined are =O or =$C(R_{18})(R_{18'})$, except when $R_{15}$ and $R_{16}$ combined are =O then $R_7$ and $R_8$ cannot both be hydrogen, and except when $R_{15}$ is attached to an $sp^2$ carbon atom in the ring, then $R_{16}$ is not present, or $R_{15}$ and $R_{16}$ together are joined in a carbocyclic 3–8 member ring.

4. A method for modulating a process mediated by androgen receptors comprising administering to a mammalian subject an amount, effective to moderate said process mediated by said androgen receptors, of a compound exhibiting activity as an androgen receptor antagonist having the formulae:

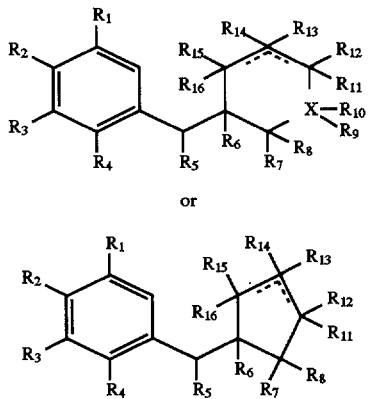

or wherein:
the dotted lines in the structure depict optional double bonds;
X is carbon;
$R_1$ is $R_{17}$, —$OR_{17}$, —$N(R_{17})(R_{17'})$, —$SR_{17}$, fluorine, chlorine, bromine, or —$NO_2$;
$R_{17}$ and ($R_{17'}$), each independently, are hydrogen, saturated or unsaturated $C_1$–$C_6$ alkyl, $C_3$–$C_7$ cycloalkyl, $C_5$–$C_7$ aryl, or $C_7$ aralkyl, said alkyl groups being branched or straight-chain;
$R_2$ is —$NO_2$, —$N(OH)R_{17}$, fluorine, chlorine, bromine, iodine, $R_{17}$, —$N(R_{17})(R_{17'})$, —$SR_{17}$, —$S(O)$—$R_{17}$, —$S(O)_2$—$R_{17}$, —$CH_2OH$, —$C(O)$—H, —$C(O)CH_3$, —$C(O)$—$OCH_3$, —$CH=CH_2$, —$CH=CH$—$C(O)$—$OCH_3$, or $R_{18}$;
$R_{18}$ and ($R_{18'}$), each independently, are hydrogen, saturated or unsaturated $C_1$–$C_6$ alkyl, $C_3$–$C_7$ cycloalkyl, $C_5$–$C_7$ aryl, or $C_7$ aralkyl, said alkyl groups being branched or straight-chain which optionally may contain hydroxyl, aldehyde, ketone, nitrile, or ester groups;

$R_3$ is $R_{17}$ or —$OR_{17}$;

$R_4$ is hydrogen, —$OR_{17}$, —$OC(O)R_{17}$, —$OC(O)OR_{17}$, —$OC(O)N(R_{17})(R_{17'})$, —$OS(O)_2R_{17}$, or —$OS(O)$—$R_{17}$, except that $R_1$, $R_2$, $R_3$, and $R_4$ cannot all be hydrogen, and $R_1$ cannot be $OCH_3$ when $R_2$, $R_3$, and $R_4$ are each hydrogen;

$R_5$ is hydrogen;

$R_6$ and $R_{17}$;

$R_7$ and $R_8$, each independently, are $R_{18}$, or $R_7$ and $R_8$ together are a carbocyclic 3–8 member ring, but $R_7$ and $R_8$ cannot both be hydrogen in the second of the two above structures;

$R_9$ and $R_{10}$, each independently, are chlorine, bromine, or $R_{17}$, or $R_9$ and $R_{10}$ combined are =O, except when X=, $R_9$ and $R_{10}$ are not present, and except that neither $R_9$ or $R_{10}$ can be bromine when $R_1$ is methoxy, $R_2$ is bromo, $R_3$ is hydrogen, $R_4$ is hydroxy, $R_5$ and $R_6$ are hydrogen, and $R_7$ and $R_8$ are methyl, $R_{11}$–$R_{14}$ are hydrogen, and $R_{15}$ and $R_{16}$ together are methylene;

$R_{11}$ and $R_{12}$, each independently, are —$OR_{17}$, $R_{18}$, are =O, or are =$CH_2$, except when $R_{11}$ is attached to an $sp^2$ carbon atom in the ring, then $R_{12}$ is not present and $R_{11}$ is $R_{18}$, or $R_{11}$ and $R_{13}$ together are joined in a carbocyclic 3–8 member ring or are —O— to form an expoxide;

$R_{13}$ and $R_{14}$, each independently, are —$OR_{17}$ or $R_{18}$, except when $R_{13}$ is attached to an $sp^2$ carbon atom in the ring, then $R_{14}$ is not present and $R_{13}$ is —$OR_{17}$ or $R_{18}$;

$R_{15}$ and $R_{16}$, each independently, are $R_{18}$ except that $R_{15}$ and $R_{16}$ cannot both be H, or $R_{15}$ and $R_{16}$ together are —$CH_2$—O— forming an epoxide, or $R_{15}$ and $R_{16}$ combined are =O or =$C(R_{18})(R_{18'})$, except when $R_{15}$ and $R_{16}$ combined are =O then $R_7$ and $R_8$ cannot both be hydrogen, and except when $R_{15}$ is attached to an $sp^2$ carbon atom in the ring, then $R_{16}$ is not present, or $R_{15}$ and $R_{16}$ together are joined in a carbocyclic 3–8 member ring.

* * * * *

UNITED STATES PATENT AND TRADEMARK OFFICE
CERTIFICATE OF CORRECTION

PATENT NO. : 5,677,336            Page 1 of 9
DATED : October 14, 1997
INVENTOR(S) : Todd K. Jones, et al.

It is certified that error appears in the above-identified patent and that said Letters Patent is hereby corrected as shown below:

Column 1, line 8, change "arc" to --are--.

Column 4, line 52, change "2Hydroxy-flutamide" to --2-Hydroxy-flutamide--.

Column 4, line 66, change "arc" to --are--.

Column 7, line 45, change "carded" to --carried--.

Column 8, line 4, change "carded" to --carried--.

Column 8, line 6, change "2-(ten-Butyl)" to --2-(*tert*-Butyl)--.

Column 8, line 15, change "rain," to --min--.

Column 8, line 26, change "(400 MHz, CDCl)" to --(400 MHz, $CDCl_3$).--.

Column 8, line 29, change "$^{13}$C. NMR" to --$^{13}$C NMR--.

Column 8, line 39, change "TLC." to --TLC--.

Column 8, line 64, change "TLC." to --TLC--.

Column 9, line 45, change "1H" to --$^1$H--.

UNITED STATES PATENT AND TRADEMARK OFFICE
CERTIFICATE OF CORRECTION

PATENT NO. : 5,677,336
DATED : October 14, 1997
INVENTOR(S) : Todd K. Jones, et al.

It is certified that error appears in the above-identified patent and that said Letters Patent is hereby corrected as shown below:

Column 11, line 46, change "TLC." to --TLC--.

Column 11, line 49, change "Edenmeyer" to --Erlenmeyer--.

Column 12, line 66, change "(tert Butyl)" to --(tert-Butyl)

Column 12, line 66, change "4-bromo" to --4'-bromo--.

Column 13, line 18, change "4'-bromo5" to --4'-bromo-5'--.

Column 13, line 30, change "hexanes lethyl" to --hexanes/ethyl --.

Column 13, line 36, change "1H" to --$^{1}$H--.

Column 13, line 44, change "1H" to --$^{1}$H--.

Column 13, line 52, change "1H" to --$^{1}$H--.

Column 13, line 56, change "(s, 1H)" to --(s, 1H, 6'-H)--.

Column 13, line 57, change "δ5 23.5 " to --δ 23.5--.

Column 13, line 64, change "methoxyphenylmethyl " to --methoxyphenyl)methyl--.

UNITED STATES PATENT AND TRADEMARK OFFICE
CERTIFICATE OF CORRECTION

PATENT NO. : 5,677,336
DATED : October 14, 1997
INVENTOR(S) : Todd K. Jones, et al.

It is certified that error appears in the above-identified patent and that said Letters Patent is hereby corrected as shown below:

Column 14, line 40, change "rain " to --min--.

Column 16, line 3, change "(tert-Butyl)" to --(*tert*-Butyl)--.

Column 16, line 3, change "dimethylsilyloxy-4-bromo" to --dimethylsilyloxy-4'-bromo--.

Column 16, line 4, change "5'methoxyphenyl]" to --5'-methoxyphenyl]--.

Column 16, line 17, change "(tert-Butyl)" to --(*tert*-Butyl)--.

Column 16, line 22, change "1H" to --$^{1}$H--.

Column 16, line 26, change "bromo-5 '" to --bromo-5'--.

Column 16, line 38, change "$NH_4C_1$" to --$NH_4Cl$--.

Column 16, line 58, change "(tert-Butyl)" to --(*tert*-Butyl)--.

Column 17, line 23, change "TLC." to --TLC--.

Column 17, line 34, change "gL" to --µL--.

Column 17, line 45, change "a 0.92" to --δ 0.92--.

UNITED STATES PATENT AND TRADEMARK OFFICE
CERTIFICATE OF CORRECTION

PATENT NO. : 5,677,336
DATED : October 14, 1997
INVENTOR(S) : Todd K. Jones, et al.

It is certified that error appears in the above-identified patent and that said Letters Patent is hereby corrected as shown below:

Column 17, line 46, change "1.84 (m, 2H)" to --1.70 (m,1H), 1.84 (m, 2H)--.

Column 18, line 57, change "2-[2tert-butyl)" to --2-[2'-*tert*-butyl]--.

Column 18, line 62, change "$NH_4C_1$" to --$NH_4Cl$--.

Column 19, line 13, change "bromo-5 '" to -- bromo-5'--.

Column 19, line 17, change "(tert-Butyl)" to --(*tert*-Butyl)--.

Column 19, line 19, change "1H" to --$^1$H--.

Column 19, line 27, change "(tert-Butyl)" to --(*tert*-Butyl)--.

Column 19, line 65, change "2 : mL" to --2 mL--.

Column 20, line 2, change "$NH_4C_1$" to --$NH_4Cl$--.

Column 20, line 28, change "lethyl" to --ethyl--.

Column 20, line 31, change "(s, 3H acetate-$CH_3$) $CH_3$" to --(s, 3H acetate-$CH_3$)--.

Column 20, line 36, change "($5R_6S$)" to --(5R6S)--.

UNITED STATES PATENT AND TRADEMARK OFFICE
CERTIFICATE OF CORRECTION

PATENT NO. : 5,677,336
DATED : October 14, 1997
INVENTOR(S) : Todd K. Jones, et al.

It is certified that error appears in the above-identified patent and that said Letters Patent is hereby corrected as shown below:

Column 20, line 41, change "gL" to --µL--.

Column 21, line 15, change "$NH_4C_1$" to --$NH_4Cl$--.

Column 22, line 21, change "(s,3H, 3-$CH_3$)" to --(s,3H, 3-$CH_3$), 2.20 (dd, 1H)--.

Column 23, line 11, change "$J_A$=5,5" to --$J_A$=5.5 --.

Column 23, line 12, change "3.30" to --2.30--.

Column 23, line 19, change "4'H" to --4'-H--.

Column 23, line 32, change "1-H" to --1H--.

Column 23, line 36, change "6-H" to --6'-H--.

Column 23, line 49, change "$NH_4C_1$" to --$NH_4Cl$--.

Column 25, line 61-62, change "(s, 1H)" to --(s, 1H, 2-H)--.

Column 26, line 24, change "880 me" to --880 mg--.

Column 26, line 28, change "$NH_4C_1$" to --$NH_4Cl$--.

UNITED STATES PATENT AND TRADEMARK OFFICE
CERTIFICATE OF CORRECTION

PATENT NO. : 5,677,336
DATED : October 14, 1997
INVENTOR(S) : Todd K. Jones, et al.

It is certified that error appears in the above-identified patent and that said Letters Patent is hereby corrected as shown below:

Column 26, line 46, change "$NH_4C_1$" to --$NH_4Cl$--.

Column 28, line 48, change "TLC." to --TLC--.

Column 28, line 64, change "400MHz 1H NMR" to --400MHz $^1$H NMR--.

Column 28, line 64, change "TLC." to --TLC--.

Column 29, line 22, change "1H" to --$^1$H--.

Column 29, line 48, change "5,50" to --5.50--.

Column 30, line 40, change " 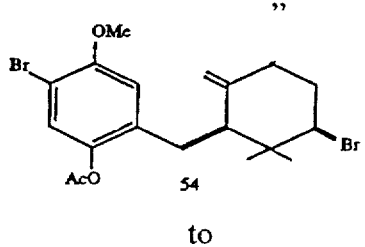 "

to

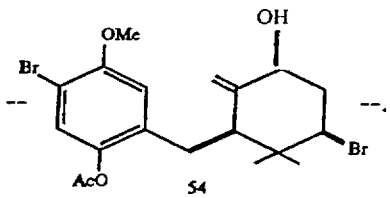 --.

UNITED STATES PATENT AND TRADEMARK OFFICE
CERTIFICATE OF CORRECTION

PATENT NO. : 5,677,336
DATED : October 14, 1997
INVENTOR(S) : Todd K. Jones, et al.

Page 7 of 9

It is certified that error appears in the above-identified patent and that said Letters Patent is hereby corrected as shown below:

Column 31, line 4, change "hexanes lethyl" to --hexanes/ethyl--.

Column 31, line 17, change "$J_{13}11.5$" to --$J\_11.5$--.

Column 31, line 39, change "hexanes lethyl" to --hexanes/ethyl--.

Column 31, line 42, change "TLC." to --TLC--.

Column 32, line 22, change "$NH_4C_1$" to --$NH_4Cl$--.

Column 32, line 35, change "1H" to --$^1H$--.

Column 39, line 1, change "at" to --al--.

Column 39, line 21, change "gl" to --$\mu l$--.

Column 41, line 29, change "carder" to --carrier--.

Column 41, line 31, change "carder" to --carrier--.

Column 41, line 35, change "carder" to --carrier--.

Column 43, line 56, change "-$N(R_{17})$" to ---$N(R_{17})(R_{17'})$--.

UNITED STATES PATENT AND TRADEMARK OFFICE
CERTIFICATE OF CORRECTION

PATENT NO. : 5,677,336
DATED : October 14, 1997
INVENTOR(S) : Todd K. Jones, et al.

Page 8 of 9

It is certified that error appears in the above-identified patent and that said Letters Patent is hereby corrected as shown below:

Column 43, line 65, change "-CH=CH-C(O) -C(O)$_3$" to ---CH=CH-C(O) -OCH$_3$--.

Column 44, line 6, change "(R$_{17}$)" to --(R$_{17'}$)--.

Column 44, line 12, change "R$_7$R$_8$" to -- R$_7$ and R$_8$--.

Column 44, line 32, change "(R$_{17}$)" to --(R$_{13}$)--.

Column 44, line 35, change "R$_6$" to --R$_{16}$--.

Column 45, line 38, change "and" to --when--.

Column 46, line 35, change "C$_5$-$_7$" to --C$_5$-C$_7$--.

UNITED STATES PATENT AND TRADEMARK OFFICE
CERTIFICATE OF CORRECTION

PATENT NO. : 5,677,336
DATED : October 14, 1997
INVENTOR(S) : Todd K. Jones, et al.

It is certified that error appears in the above-identified patent and that said Letters Patent is hereby corrected as shown below:

Column 48, line 13, change "and" to --is--.

Column 48, line 21, change "X=" to --X=0--.

Signed and Sealed this

Third Day of August, 1999

Attest:

Q. TODD DICKINSON

Attesting Officer

Acting Commissioner of Patents and Trademarks